(12) United States Patent
Cai et al.

(10) Patent No.: US 7,955,484 B2
(45) Date of Patent: Jun. 7, 2011

(54) GLUCOSE BIOSENSOR AND METHOD

(75) Inventors: Xiaohua Cai, Needham, MA (US); Chung Chang Young, Weston, MA (US); Jianhong Pei, Boxborough, MA (US); Andy Vo, Sommerville, MA (US)

(73) Assignee: Nova Biomedical Corporation, Waltham, MA (US)

( * ) Notice: Subject to any disclaimer, the term of this patent is extended or adjusted under 35 U.S.C. 154(b) by 1177 days.

(21) Appl. No.: 11/306,005

(22) Filed: Dec. 14, 2005

(65) Prior Publication Data

US 2007/0131549 A1    Jun. 14, 2007

(51) Int. Cl.
*G01N 27/327* (2006.01)
*G01N 27/416* (2006.01)

(52) U.S. Cl. .............. 204/403.04; 204/403.11
(58) Field of Classification Search ......... 204/403.01–403.15; 205/777.5, 205/792
See application file for complete search history.

(56) References Cited

U.S. PATENT DOCUMENTS

| | | |
|---|---|---|
| 4,515,889 A | 5/1985 | Klose et al. |
| 4,545,382 A | 10/1985 | Higgins et al. |
| 4,605,629 A | 8/1986 | Lange et al. |
| 4,711,245 A | 12/1987 | Higgins et al. |
| 4,758,323 A | 7/1988 | Davis et al. |
| 4,923,796 A | 5/1990 | Deneke et al. |
| 4,929,545 A | 5/1990 | Freitag |
| 5,236,567 A | 8/1993 | Nanba et al. |
| 5,306,413 A * | 4/1994 | Hayashi et al. ............ 204/403.1 |
| 5,334,508 A | 8/1994 | Hoenes |
| 5,380,649 A | 1/1995 | Berry et al. |
| 5,405,511 A | 4/1995 | White et al. |
| 5,484,708 A | 1/1996 | Hoenes et al. |
| 5,501,958 A | 3/1996 | Berry et al. |
| 5,509,410 A | 4/1996 | Hill et al. |
| 5,521,060 A | 5/1996 | Hoenes et al. |
| 5,543,299 A | 8/1996 | Diebold et al. |
| 5,583,006 A | 12/1996 | Storhoff et al. |
| 5,682,884 A | 11/1997 | Hill et al. |
| 5,762,770 A | 6/1998 | Pritchard et al. |
| 5,820,551 A | 10/1998 | Hill et al. |
| 5,846,837 A | 12/1998 | Thym et al. |
| 5,858,691 A | 1/1999 | Hoenes et al. |
| 5,997,817 A | 12/1999 | Crismore et al. |

(Continued)

FOREIGN PATENT DOCUMENTS

EP    1 146 332 A1    10/2001

(Continued)

OTHER PUBLICATIONS

Jin et al., "PQQ as redox shuttle for quinoprotein glucose dehydrogenase," Biol. Chem., 1998,1207-11, 379.

(Continued)

*Primary Examiner* — Ula C Ruddock
*Assistant Examiner* — Gurpreet Kaur
(74) *Attorney, Agent, or Firm* — Robert R. Deleault, Esq; Mesmer & Deleault, PLLC

(57) ABSTRACT

A system for more accurately measuring glucose in a sample includes a first glucose-sensing electrode incorporating a quantity of glucose oxidase, a second glucose-sensing electrode incorporating a quantity of PQQ-glucose dehydrogenase, a reference electrode, and means for selecting between a first glucose measurement made with the first glucose-sensing electrode and a second glucose measurement made with the second glucose-sensing electrode.

15 Claims, 16 Drawing Sheets

U.S. PATENT DOCUMENTS

| | | |
|---|---|---|
| 6,057,120 A | 5/2000 | Heindl et al. |
| 6,103,033 A | 8/2000 | Say et al. |
| 6,103,509 A | 8/2000 | Sode et al. |
| 6,134,461 A | 10/2000 | Say et al. |
| 6,143,164 A | 11/2000 | Heller et al. |
| 6,193,873 B1 | 2/2001 | Ohara et al. |
| 6,299,757 B1 * | 10/2001 | Feldman et al. .............. 205/775 |
| 6,338,780 B2 | 1/2002 | Feldman et al. |
| 6,447,657 B1 | 9/2002 | Bhullar et al. |
| 6,461,496 B1 | 10/2002 | Feldman et al. |
| 6,475,372 B1 | 11/2002 | Ohara et al. |
| 6,484,046 B1 | 11/2002 | Say et al. |
| 6,488,828 B1 | 12/2002 | Bhullar et al. |
| 6,540,890 B1 | 4/2003 | Bhullar et al. |
| 6,551,494 B1 | 4/2003 | Heller et al. |
| 6,562,210 B1 | 5/2003 | Bhullar et al. |
| 6,565,509 B1 | 5/2003 | Say et al. |
| 6,576,101 B1 | 6/2003 | Heller et al. |
| 6,576,102 B1 | 6/2003 | Rappin et al. |
| 6,579,690 B1 | 6/2003 | Bonnecaze et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,618,934 B1 | 9/2003 | Feldman et al. |
| 6,645,359 B1 | 11/2003 | Bhullar et al. |
| 6,656,702 B1 | 12/2003 | Yugawa et al. |
| 6,676,815 B1 | 1/2004 | Bhullar et al. |
| 6,676,816 B2 | 1/2004 | Mao et al. |
| 6,749,740 B2 | 6/2004 | Liamos et al. |
| 6,767,440 B1 | 7/2004 | Bhullar et al. |
| 6,773,564 B1 | 8/2004 | Yugawa et al. |
| 6,797,150 B2 | 9/2004 | Kermani et al. |
| 6,814,644 B2 | 11/2004 | Bhullar et al. |
| 6,814,843 B1 | 11/2004 | Bhullar et al. |
| 2002/0084196 A1 | 7/2002 | Liamos et al. |
| 2002/0100684 A1 | 8/2002 | Bhullar et al. |
| 2002/0148739 A2 | 10/2002 | Liamos et al. |
| 2002/0157947 A1 | 10/2002 | Rappin et al. |
| 2002/0157948 A2 | 10/2002 | Liamos et al. |
| 2002/0192115 A1 | 12/2002 | Bhullar et al. |
| 2003/0088166 A1 | 5/2003 | Say et al. |
| 2003/0094367 A1 | 5/2003 | Bhullar et al. |
| 2003/0094383 A1 | 5/2003 | Kermani et al. |
| 2003/0094384 A1 | 5/2003 | Vreeke et al. |
| 2003/0096997 A1 | 5/2003 | Mao et al. |
| 2003/0098233 A1 | 5/2003 | Kermani et al. |
| 2003/0100040 A1 | 5/2003 | Bonnecaze et al. |
| 2003/0100821 A1 | 5/2003 | Heller et al. |
| 2003/0104595 A1 | 6/2003 | Kratzch et al. |
| 2003/0116447 A1 | 6/2003 | Surridge et al. |
| 2003/0148169 A1 | 8/2003 | Willner et al. |
| 2003/0155237 A1 | 8/2003 | Surridge et al. |
| 2003/0175841 A1 | 9/2003 | Watanabe et al. |
| 2003/0178302 A1 | 9/2003 | Bhullar et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0201176 A1 | 10/2003 | Mills et al. |
| 2003/0201178 A1 | 10/2003 | Rappin et al. |
| 2003/0201194 A1 | 10/2003 | Heller et al. |
| 2003/0228681 A1 | 12/2003 | Ritts et al. |
| 2003/0232418 A1 | 12/2003 | Takeshima et al. |
| 2004/0005683 A1 | 1/2004 | Kratzsch et al. |
| 2004/0031682 A1 | 2/2004 | Wilsey |
| 2004/0054267 A1 | 3/2004 | Feldman et al. |
| 2004/0055898 A1 | 3/2004 | Heller et al. |
| 2004/0060818 A1 | 4/2004 | Feldman et al. |
| 2004/0065562 A1 | 4/2004 | Hodges |
| 2004/0094413 A1 | 5/2004 | Bhullar et al. |
| 2004/0144644 A1 | 7/2004 | Bhullar et al. |
| 2004/0163953 A1 | 8/2004 | Bhullar et al. |
| 2004/0167801 A1 | 8/2004 | Say et al. |
| 2004/0171921 A1 | 9/2004 | Say et al. |
| 2004/0191883 A1 | 9/2004 | Sode et al. |
| 2004/0194302 A1 | 10/2004 | Bhullar et al. |
| 2004/0200721 A1 | 10/2004 | Bhullar et al. |
| 2004/0206625 A1 | 10/2004 | Bhullar et al. |
| 2004/0225230 A1 | 11/2004 | Liamos et al. |
| 2004/0236200 A1 | 11/2004 | Say et al. |
| 2004/0245101 A1 | 12/2004 | Willner et al. |
| 2004/0245121 A1 | 12/2004 | Nagakawa et al. |
| 2004/0249254 A1 | 12/2004 | Racchini et al. |
| 2004/0265828 A1 | 12/2004 | Sode et al. |
| 2005/0008537 A1 | 1/2005 | Mosoiu et al. |
| 2005/0013731 A1 | 1/2005 | Burke et al. |
| 2005/0164322 A1 | 7/2005 | Heller et al. |

FOREIGN PATENT DOCUMENTS

| | | |
|---|---|---|
| EP | 1 308 720 A1 | 5/2003 |

OTHER PUBLICATIONS

Okuda et al., "Glucose enzyme electrode using cytochrome b(562) as an electron mediator," Biosens. & Bioelectron., 2003, 699-704, 18.

Wens et al., "A previously undescribed side effect of icodextrin: overestimation of glycemia by glucose analyzer," Petit. Dial. Int., 1998, 603-9, 18.

Schmidt, "Oxygen-independent oxidases: a new class of enzymes for application in diagnostics," Clin. Chim. Acta., 1997, 33-7, 266.

Clark et al., "Rapid micromeasurement of lactate in whole blood," Crit. Care Med., 1984, 461-4, 12(5).

Aziz et al., "Comparative study of home blood glucose monitoring devices: Visidex, Chemstrip bG, Glucometer, and Accu-Chek bG," Diabetes Care, 1983, 529-32, 6(6).

Tanaka et al., "Increasing stability of water-soluble PQQ glucose dehydrogenase by increasing hydrophobic interaction at dimeric interface," BMC Biochem., 2005, 6(1).

Mullen et al., "Enzyme electrode for glucose based on the quinoprotein glucose dehydrogenase," Analyst, 1985, 925-8, 110.

D'Costa et al., "Quinoprotein glucose dehydrogenase and its application in an amperometric glucose sensor," Biosensors, 1986, 71-87, 2.

Matsushita et al., "Quinoprotein D-glucose dehydrogenase of the Acinetobacter calcoaceticus respiratory chain . . . " Biochemistry, 1989, 6276-80, 28.

Matthews et al., "X-Ray Crystallographic studies of quinoproteins," Principles and Applications of Quino Proteins, 1992, 245-73, Marcell Dekker, New York.

Kilpatrick et al., "Variations in sample pH and PO2 affect ExacTech meter glucose measurements," Diabet. Med., 1993, 506-9, 11.

Boguslavsky et al., "Amperometric thin film biosensors based on gluscose dehydrogenase . . . " Biosens. Bioelectron, 1995, 693-704, 10.

Yao et al., "Electrochemical dehydrogenase-based homogeneous assays in whole blood," Clin. Chem., 1995, 591-8, 41.

Cross et al., "Blood glucose reagent strip tests in the operating room . . . " J. Clin. Monit., 1996, 27-33, 12.

Wingard et al., "Immobilized enzyme electrodes for the potentiometric measurement of glucose concentration . . . " J. Biomed. Mater. Res., 1997, 921-935, 13.

Curulli et al., "Assembling and evaluation of new dehydrogenase enzyme electrode probe . . . " Biosens. Bioelectron, 1997, 1043-55, 12.

Zhang et al, "Dual-enzyme fiber optic biosensor for pyruvate," Anal. Chim. Acta, 1997, 59-65, 35.

Kost et al., "Multicenter study of oxygen-insensitive handheld glucose point-of-care testing . . . " Crit. Care Med., 1998, 581-90, 36.

Ervin et al., "Issues and implications in the selection of blood glucose monitoring technologies," Diabetes Technology & Therapeutics, 1999, 3-11, 1.

Laurinavicius et al., "Oxygen insensitive glucose biosensor based on PQQ-dependent glucose dehydrogenase," Anal. Lett., 1999, 299-316, 32.

Dewanti et al., "Ca+2-assisted, direct hydride transfer and rate-determining tautomerization of C5-reduced PQQ to PQQH2 . . . " Biochemistry, 2000, 9384-92, 39.

Duine, "The PQQ story," J. Biosci. Bioeng., 1999, 231-6, 88.

Habermueller et al., "An oxygen-insensitive reagentless glucose biosensor based on osmium-complex modified polypyrrole," Electroanalysis, 2000, 1383-89, 12.

Inoue et al., "Electrochemical detection of thiols with a coenzyme pyrroloquinoline quinone modified electrode," Anal. Chem., 2000, 5755-60, 72.

Jones et al., "Dynamic change in glucose and lactate in the cortex of the freely moving rat monitored using microdialysis," J. Neurochemistry, 2000, 1703, 75.

Razumiene et al., "4-Ferrocenylphenol as an electron transfer mediator in PQQ-dependent alcohol . . ." Electrochem. Commun., 2000, 307-11, 2.

Tang et al., "Oxygen effects on glucose measurements with a reference analyzer and three handheld meters," Diabetes Technol. Ther., 2000, 349-62, 2.

Gouda et al., "Optimization of the multienzyme system for sucrose biosensor by response surface methodology," World J. of Microbio. and Biotech., 2001, 595-600, 17.

Quinto, "Enzyme modified microband electrodes: cross-talk effects and their elimination," Analyst, 2001, 1068-72, 126.

Razumiene et al., "Amperometric detection of glucose and ethanol in beverages using flow cell . . ." Sen. Actuators, 2001, 243-48, 78.

Rose et al., "Quinoprotein glucose dehydrogenase modified thick-film electrodes for the amperometric detection . . ." Fresenuis J. Anal. Chem., 2001, 145-52, 369.

Choubtum, "Accuracy of glucose meters in measuring low blood glucose levels," J. Med. Assoc. Thai., 2002, S1104-10, 85 Suppl., 4.

Kasai, "Simultaneous detection of uric and glucose on a dual-enzyme chip using scanning electrochemical microscopy . . ." Anal Chim. Acta, 2002, 263-70, 458.

Laurinavicius et al., "Bioelectrochemical application of some PQQ-dependent enzymes," Bioelectrochemistry, 2002, 29-32, 55.

Mano et al., "Affinity assembled multilayers for new dehydrogenase biosensors," Bioelectrochemistry, 2002, 123-6, 56.

Nistor et al., "A glucose dehydrogenase biosensor as an additional signal amplification step in an enzyme-flow immunoassay," Analyst, 2002, 1076-81, 127.

Ge et al., "Genetically engineered binding proteins as biosensors for fermentation and cell culture," Biotech. and Bioeng., 2003, 723-31, 84.

Razumiene et al., "New bioorganometallic ferrocene derivatives as mediators for glucose and ethanol biosensors . . ." J. Organometal. Chem., 2003, 83-90, 668.

Shi et al., "On-line biosensor for simultaneous determination of glucose, choline, and glutamate integrated with a microseparation system," Electrophoresis, 2003, 3266-72, 42.

Wang et al., "Carbon nanotube/teflon composite electrochemical sensors and biosensor," Anal. Chem., 2003, 2075-9, 75.

Yamashita et al., "Electrochemical behavior of pyrroloquinoline quinone immobilized on silica gel . . ." J. Colloid Interface Sci., 2003, 99-105, 263.

Campuzano et al., "An integrated bienzyme glucose oxidase-fructose dehydrogenase-tetrathiafulvalene-3-mercaptopropionic . . ." Bioelectrochemistry, 2004, 199-206, 63.

Castillo et al., "Biosensors for life quality—design, development, and applications," Sensors and Actuators B, 2004, 179-94, 102.

Laurinavicius et al., "Wiring of PQQ-dehydrogenases," Biosens Bioelectron., 2004, 1217-22, 20.

Okuda et al., "PQQ glucose dehydrogenase with novel electron transfer ability," Biochem. Biophys. Res. Commun., 2004, 793-7, 314.

Zhang et al., "Carbon nanotube-chitosan system for electrochemical sensing based on dehydrogenase enzymes," Anal. Chem., 2004, 5045-50, 76.

Suprun et al., "Bi-enzyme sensor based on thick-film carbon electrode modified with electropolymerized tyramine," Bioelectrochemistry, 2004, 281-4, 63.

Kulkarni et al., "Analysis of blood glucose measurements using capillary and arterial blood samples in intensive care patients," Intensive Care Med., 2005, 142-45, 31.

* cited by examiner

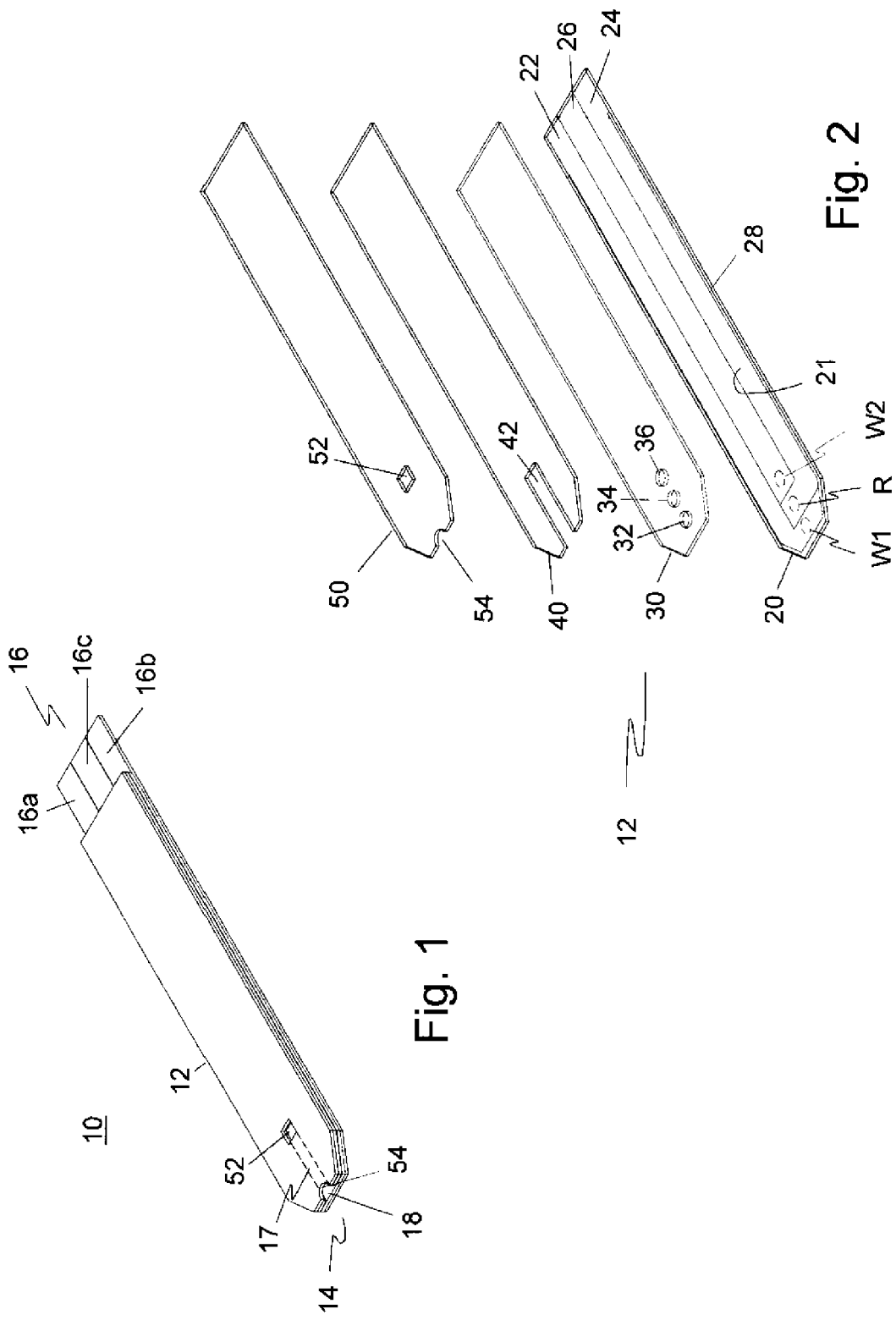

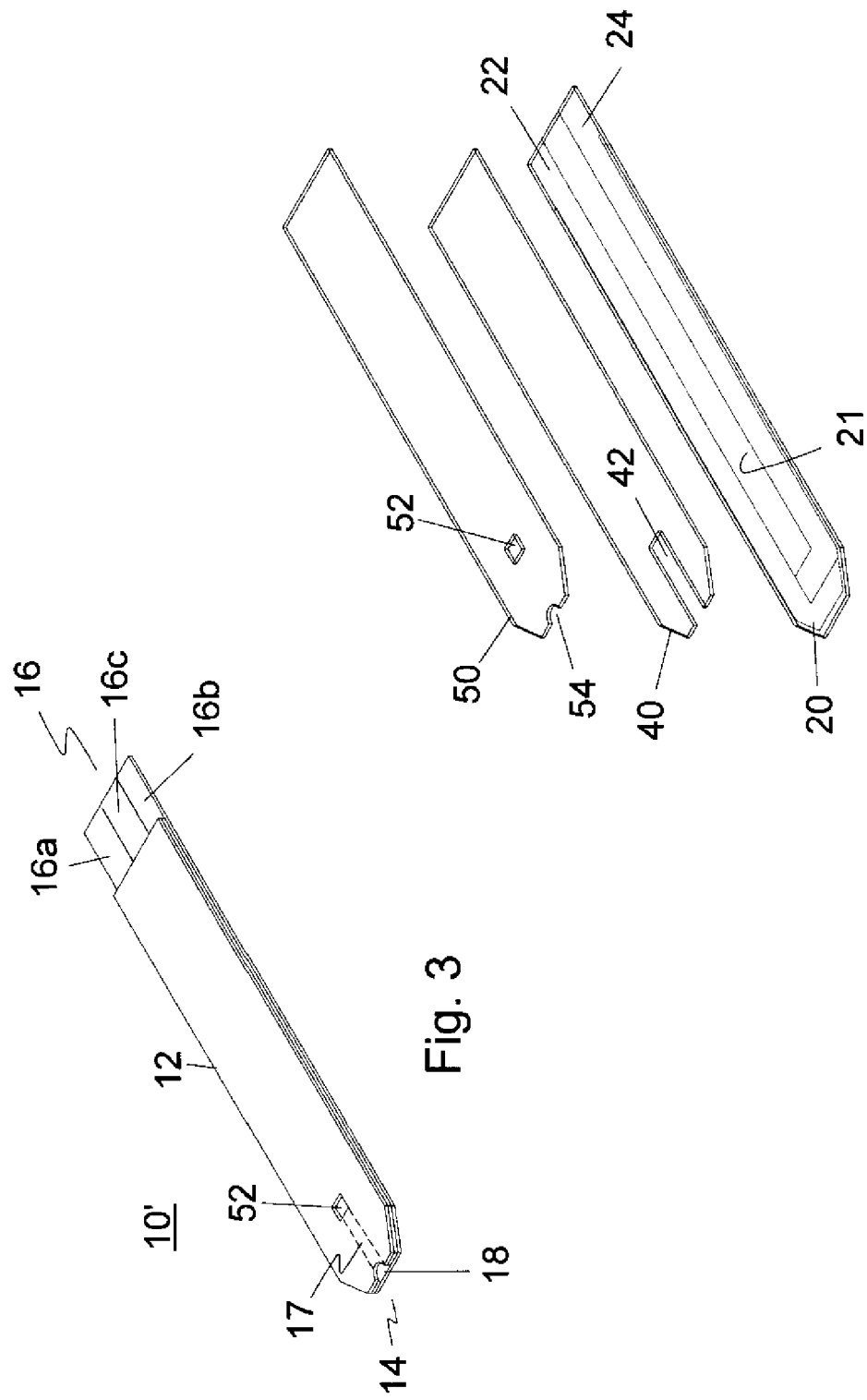

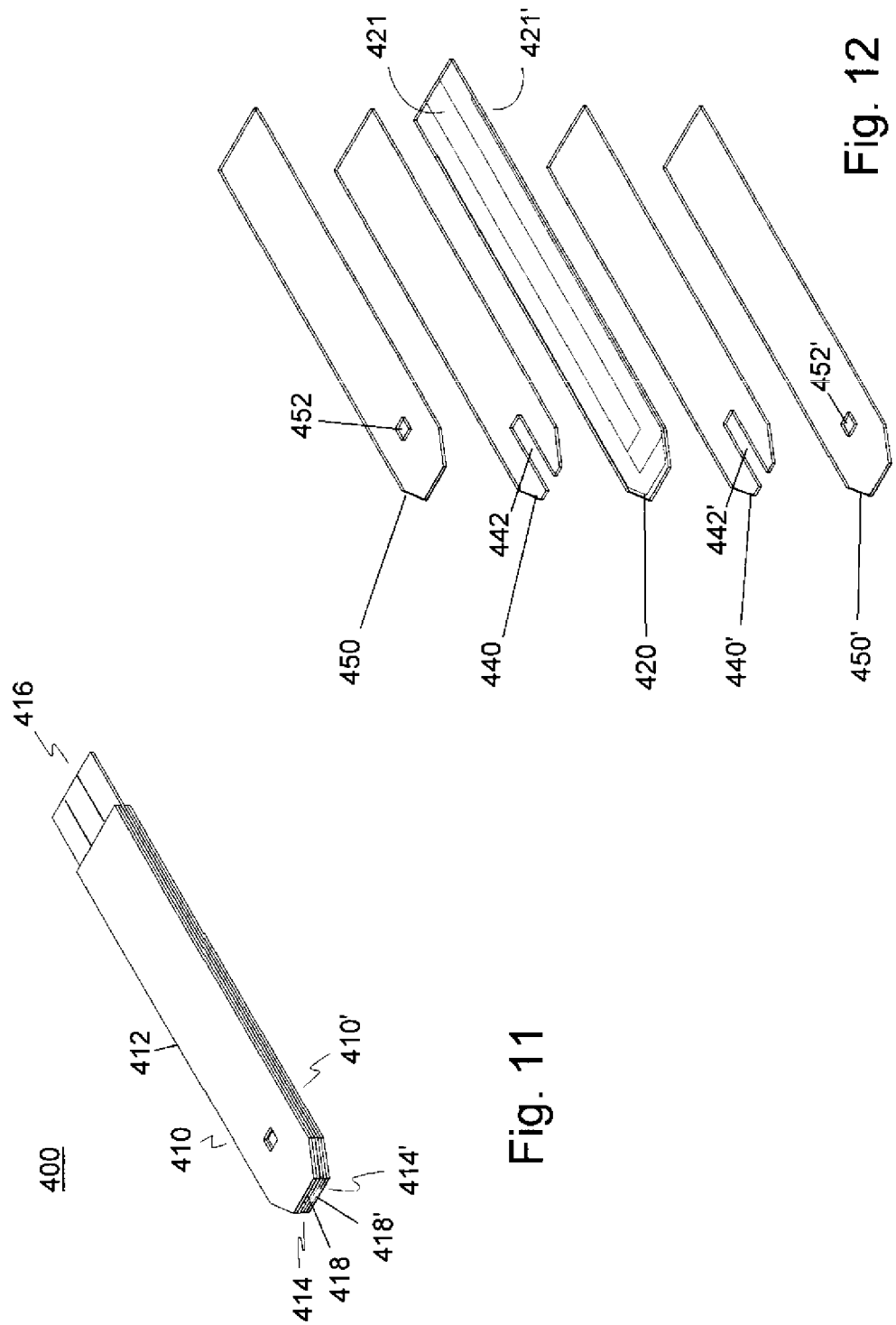

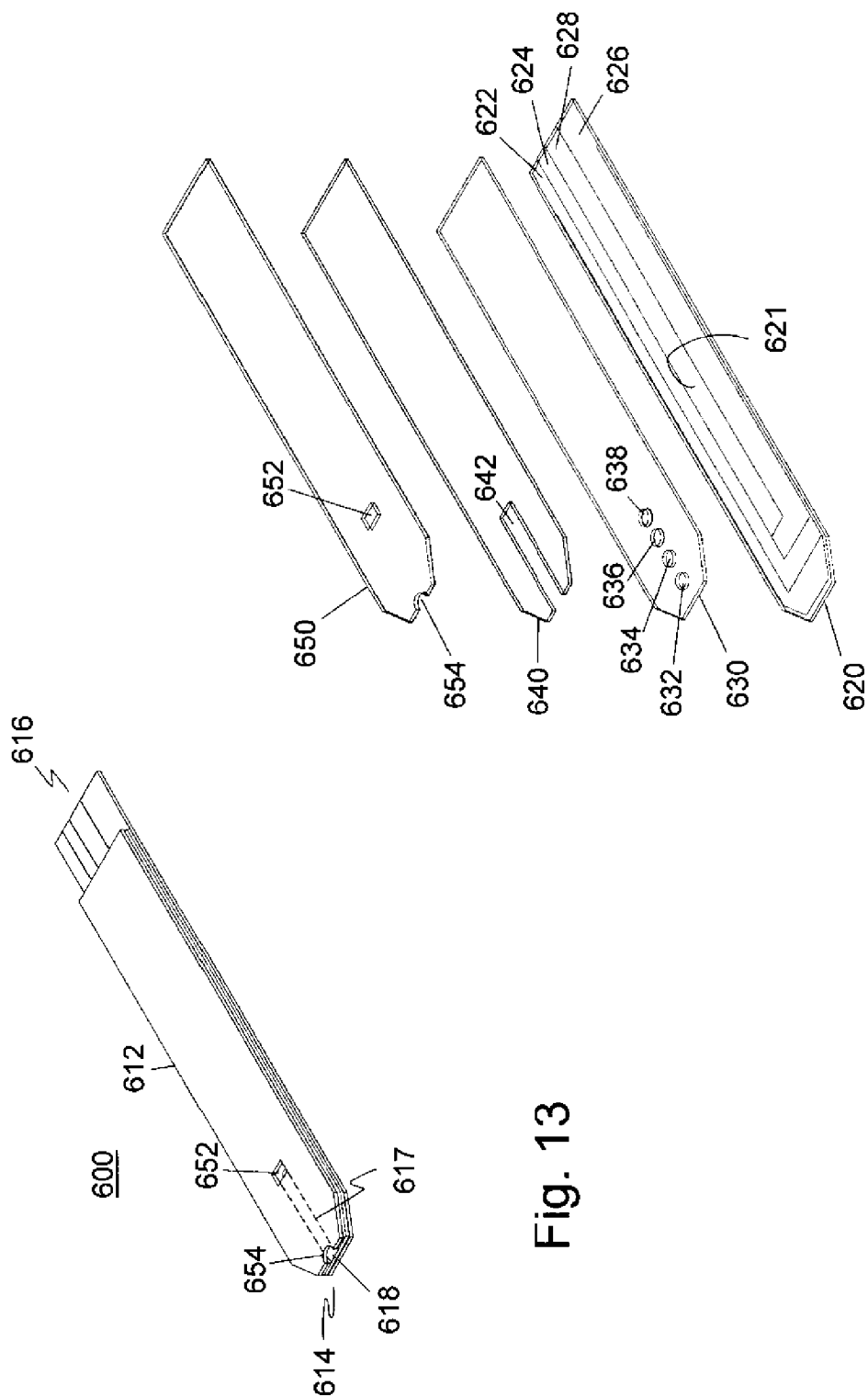

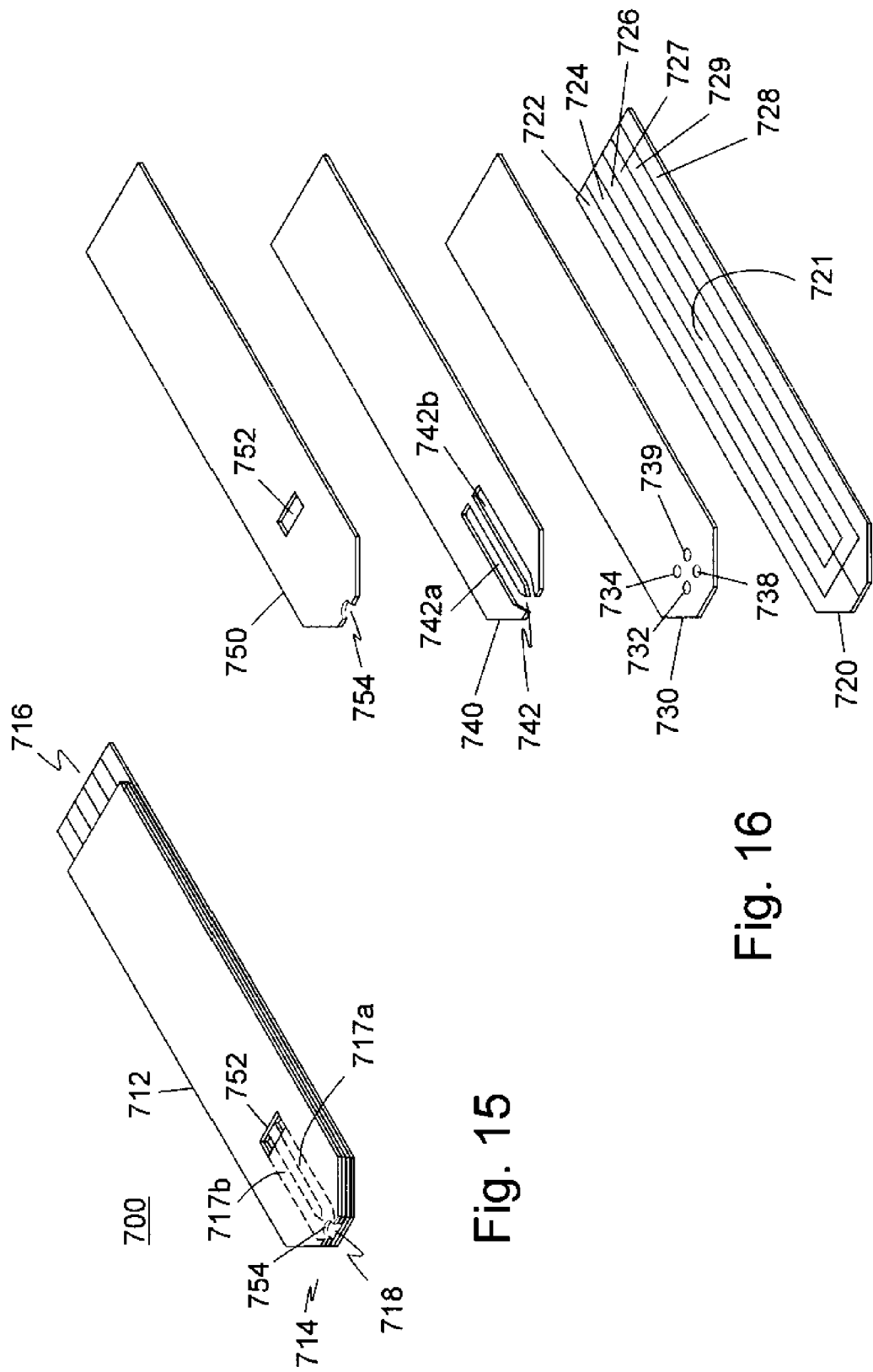

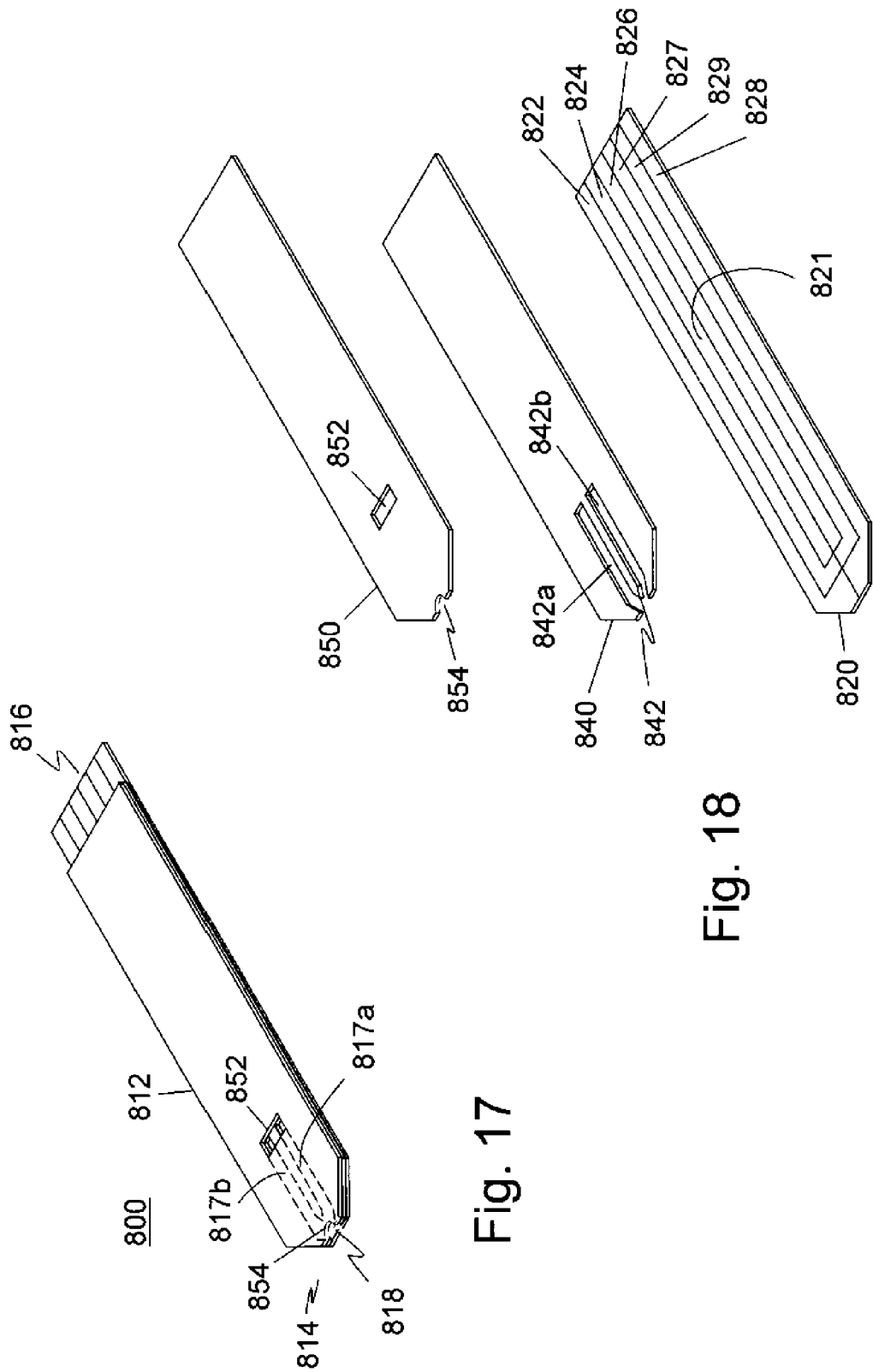

GLUCOSE BIOSENSOR AND METHOD

BACKGROUND OF THE INVENTION

1. Field of the Invention

The present invention relates to a biosensor for the detection of glucose present in biological fluids such as blood. Particularly, the present invention relates to a biosensor for the amperometric detection of glucose in biological fluids. More particularly, the present invention relates to a biosensor having high accuracy for the amperometric detection of glucose in biological fluids.

2. Description of the Prior Art

It is well known that diabetes is a major health concern. As a general rule, the American Diabetes Association (ADA) recommends that most patients with type I (insulin-dependent) diabetes test glucose three or more times per day. Insulin controls utilization of glucose or sugar in the blood and prevents hyperglycemia which, if left uncorrected, can lead to ketosis. Improper administration of insulin therapy, however, can result in hypoglycemic episodes. Hypoglycemia can cause coma and can be fatal.

Hyperglycemia in diabetics has been correlated with several long-term effects of diabetes such as heart disease, atherosclerosis, blindness, stroke, hypertension and kidney failure. The amount of the insulin injection is related to the blood glucose level. Therefore, the accurate detection of blood glucose is vital for the proper treatment of diabetes. Patients with Type II (non-insulin-dependent) diabetes can also benefit from accurate blood glucose monitoring in the control of their condition by way of diet and exercise.

Since the introduction of the home-use glucose strip and hand-held detection device or meter in the late 1970's, the treatment of diabetes has been greatly improved. However, inaccurate test results inherent in prior glucose measuring systems can lead to the improper treatment of diabetes from time to time. One of the major reasons for inaccurate test results is related to the chemical reagents applied to the glucose strips. Most glucose strips on the market are biosensors based on the use of a mediator and either glucose oxidase (GOD) or pyrroloquinoline quinone dependent glucose dehydrogenase (PQQ-GDH).

The mediator/GOD-based biosensors extend the linear response range for glucose, as compared to the non-mediator based biosensors (hydrogen peroxide measurement is involved). Oxygen-related drawbacks, however, still exist. Mediators are not as efficient at shuttling electrons with the enzyme as is the oxygen molecule. In fact, any oxygen in the sample solution can compete more effectively than the mediators for the enzyme site. The measurements with the mediator/GOD-based biosensors show significantly lower results with increasing oxygen partial pressure ($pO_2$) in the fluid samples. The inaccurate testing results caused by varying oxygen concentration were extensively investigated by several groups (T. Y. Chun, M. Hirose, T. Sawa, M. Harada, T. Hosokawa, Y. Tanaka and M. Miyazaki, Anesth Analg., 75, 993-7, 1994; J. H. Lee, H. Vu, G. J Kost, Clinical Chemistry, 42, S163, 1996; K. Kurahashi, H. Maryta, Y. Usuda and M. Ohtsuka, Crit. Care Med., 25, 231-235, 1997; Z. Tang, R. F. Louie, M. Payes, K. Chang and G. J. Kost, Diabetes Technology & Therapeutics, 2, 349-362, 2000). As warned by Tang et al. (Z. Tang, R. F. Louie, J. H. Lee, D. M. Lee, E. E. Miller, and G. J. Kost, Crit. Care Med., 29, 1062-1070, 2001), special caution should be taken when using the glucose strips for point-of-care glucose testing in critically ill and other patients with unpredictable blood $pO_2$ level.

Additionally, biological specimens contain widely varying oxygen levels. The typical oxygen partial pressure of a venous blood sample is about 32±7 mmHg. In some cases, it can be as low as 20 mmHg. For an arterial sample, one can expect much higher oxygen levels. For the patients who are in o oxygen therapy, the level of arterial $pO_2$ can reach as high as 700 mmHg. Thus, the mediator/GOD-based biosensors could give inaccurate testing results due to the different oxygen concentrations. This becomes more serious when the glucose concentration is at a low level (e.g. glucose concentration less than 70 mg/dL).

To obviate the interference resulting from varying oxygen concentration or so-called "oxygen effect" associated with the use of glucose oxidase, glucose dehydrogenase (GDH) was recently used to replace the oxygen-sensitive glucose oxidase. Glucose dehydrogenase, whose coenzyme is pyrroloquinoline quinone (PQQ), does not interact with oxygen. Therefore, the resultant glucose sensor is unaffected by variable oxygen concentration in the sample. A few products have been developed and marketed using this enzyme such as, for example, Accu-Chek™ Comfort Curve®, Roche Diagnostics, IN, USA, Freestyle®, TheraSense, Alameda, Calif., USA and Ascensia®, Bayer Health Care, Mishawaka, Ind., USA.

The use of glucose dehydrogenase does overcome the problems caused by the oxygen effect. However, glucose dehydrogenase is not as specific as glucose oxidase. It not only reacts with glucose but also reacts with other sugars like galactose and maltose. Both galactose and maltose have a similar structure to glucose. Maltose is composed of two glucose units and galactose differs in structure from glucose only in the position of the hydroxyl group on carbon no. 4. Severe interference can be expected. As a matter of fact, the GDH-based biosensors are more sensitive to maltose and have no discrimination between glucose and galactose (J. D. Newman, C. A. Ramsden, N. D. H. Balazs, Clinical Chemistry, 48, 2071, 2002).

A falsely high glucose reading may be obtained by patients if test strips use a glucose dehydrogenase pyrroloquinoline quinone as the enzyme method. For this reason, the Centers for Medicare & Medicaid Services and ESRD Networks were alerted by the Food and Drug Administration (FDA) on Apr. 18, 2003, to a concern with peritoneal dialysis patients' glucose readings while on Icodextrin Extraneal dialysis solution and the effects of falsely elevated glucose readings because of the interaction of maltose. A false high blood glucose reading could cause a patient to be given more insulin than needed. This, in turn, can lower a patient's blood sugar unnecessarily and can cause a serious reaction including loss of consciousness.

Therefore, what is needed is a glucose measuring system that can provide a more accurate blood glucose reading. What is also needed is a glucose measuring system that can provide a more accurate blood glucose reading by reducing inaccurate test results caused by varying oxygen partial pressure in the fluid sample. What is further needed is a glucose measuring system that can provide a more accurate blood glucose reading by reducing inaccurate test results caused by other sugars in the fluid sample. What is still further needed is a disposable glucose sensor capable of providing more accurate blood glucose readings.

SUMMARY OF INVENTION

It is an object of the present invention to provide a glucose sensor system that provides glucose readings, which minimize interference from dissolved oxygen and from maltose and galactose present in the fluid samples. It is another object of the present invention to provide a disposable glucose sensor, which can be used for capillary blood testing at finger or alternative sites such as the upper arm, forearm, base of the thumb, and thigh. It is a further object of the present invention to provide a glucose sensor for venous blood testing and for arterial and venous blood testing. It is still another object of the present invention to provide a disposable glucose sensor that requires a small amount of blood sample and still achieves accurate results.

The present invention achieves these and other objectives by incorporating two glucose electrodes, each incorporating a different enzyme for measuring glucose, and selecting the appropriate electrode response to determine the glucose concentration in a fluid sample. The two enzymes are glucose oxidase (GOD) and a quinoprotein glucose dehydrogenase (GDH), more specifically known as pyrroloquinoline quinone dependent glucose dehydrogenase (PQQ-GDH). Both glucose (i.e. working) electrodes respond to the glucose concentration over the entire linear range. If the sample has a lower level of $pO_2$, the GOD-based working electrode will give higher response while the GDH-based working electrode gives an accurate result. Thus, the preferred response should be from the GDH-based working electrode. In the case where the sample contains maltose or galactose, the GDH-based working electrode will show higher response while the GOD-loaded working electrode gives an accurate result. The preferred response should be from the GOD-loaded working electrode. The selection process is preferably done automatically when the glucose electrode readings are automatically fed into a preprogrammed meter.

The glucose sensor of the present invention incorporates several embodiments including, but not limited to, a 4-layer construction and a 3-layer construction as disclosed in U.S. Pat. Nos. 6,767,441, 6,287,451, 6,258,229, 6,837,976, and 6,942,770, all of which are incorporated herein by reference.

In the first embodiment of the present invention, the glucose sensor uses a 4-layer laminated construction.

In one aspect of the first embodiment, the glucose sensor has a laminated, elongated body having a sample fluid channel, which forms a substantially flat sample chamber, connected between an opening on one end of the laminated body and a vent hole spaced from the opening. Within the fluid channel lie at least two working electrodes and a reference/counter electrode. The arrangement of the two or more working electrodes and the reference electrode is not important for purposes of the results obtained from the sensor. The working electrodes and the reference electrode are each in electrical contact with separate conductive paths. The separate conductive paths terminate and are exposed for making an electrical connection to a reading device on the end opposite the sample entrance end of the laminated body.

In another aspect of the first embodiment, the laminated body has a base layer made from a plastic material. Several conductive paths are delineated on the base layer. The conductive paths may be deposited on the insulating layer by screen printing, by vapor deposition, or by any method that provides for a conductive layer that adheres to the base layer. The conductive paths may be individually disposed on the insulating layer, or a conductive layer may be disposed on the insulating layer followed by etching/scribing the required number of conductive paths. The etching process may be accomplished chemically, by mechanically scribing lines in the conductive layer, by using a laser to scribe the conductive layer into separate conductive paths, or by any means that will cause a break between and among the separate conductive paths required by the present invention. Conductive coatings or layers that may be used are coatings of copper, gold, tin oxide/gold, palladium, other noble metals or their oxides, or carbon film compositions. The preferred conductive coatings are gold film or a tin oxide/gold film composition.

In a further aspect of the first embodiment of the present invention, the laminated body has a first middle insulating layer, also called a reagent holding or electrode area defining layer, on top of the base layer and the conductive paths. The reagent holding layer, or reagent holding layer, contains at least two openings for two or more working electrodes and a reference electrode. Each opening corresponds to and exposes a small portion of a single conductive path. The openings for the working electrodes are substantially the same size. The opening for the reference electrode may be the same or different size as the openings for the working electrodes. The placement of all of the openings is such that they will all be all positioned within the sample fluid channel described above. The reagent holding layer is also made of an insulating dielectric material, preferably plastic, and may be made by die cutting the material mechanically or with a laser and then fastening the material to the base layer. An adhesive, such as a pressure-sensitive adhesive, may be used to secure the first middle insulating layer to the base layer. Adhesion may also be accomplished by ultrasonically bonding the reagent holding layer to the base layer. The reagent holding layer may also be made by screen printing an insulating material or by binding a photopolymer over the base layer.

In yet another aspect of the first embodiment, the laminated body also has a second middle insulating layer, also called a channel-forming layer, on top of the reagent holding layer. The channel forming layer is also made of a plastic insulating material and creates the sample chamber of the laminated body. It contains a U-shaped opening on one end which overlays the openings on the reagent holding layer with the open end corresponding to the sample entrance end of the laminated body described earlier. A double coated, pressure-sensitive adhesive tape may be used as the channel forming layer.

In yet another aspect of the first embodiment, the laminated body of the present invention has a cover with a vent opening and an entrance notch. The vent opening is located such that at least a portion of the vent opening overlays the base of the U-shaped cutout of the channel forming layer. The vent allows air within the sample fluid channel to escape as the sample fluid enters the sample entrance or sample inlet of the laminated body. The notch is located at the sample entrance end. The sample fluid generally fills the sample chamber by capillary action. In small volume situations, the extent of capillary action is dependent on the hydrophobic/hydrophilic nature of the surfaces in contact with the fluid undergoing capillary action. Capillary forces are enhanced by either using a hydrophilic insulating material to form the cover, or by coating at least a portion of one side of a hydrophobic insulating material with a hydrophilic substance in the area of the cover that faces the sample chamber between the open end of the laminated body and the vent opening of the cover. It should be understood that an entire side of the cover may be coated with the hydrophilic substance and then bonded to the channel forming layer.

In yet another aspect of the first embodiment, one opening contains electrode material for the first working electrode (W1) loaded with GOD, a mediator and other indigents, one for the second working electrode (W2) loaded with pyrroloquinoline quinone dependent glucose dehydrogenase (PQQ-GDH), a mediator and other indigents, and one for the reference electrode (R). The positional arrangement of the working electrodes and the reference electrode in the channel is not critical for obtaining usable results from the electrochemical sensor. The possible electrode arrangements within the sample fluid channel may be W1-W2-R, W1-R-W2, R-W1-W2, W2-W1-R, W2-R-W1, or R-W2-W1, with the arrangement listed as the electrodes would appear from the sample entrance of the laminated body to the vent opening. The preferred position was found to be W1-W2-R; that is, as the sample fluid entered the open end of the laminated body, the fluid would cover W1 first, then W2, then R. The preferred position obviates reliability and accuracy problems due to an insufficient sample fluid size. The working electrodes and the reference electrode are each in electric contact with separate conductive paths, respectively. The separate conductive paths terminate and are exposed for making an electrical connection to a reading device on the end opposite of the sample entrance end of the laminated body.

In a further aspect of the first embodiment, the working electrodes are loaded with a mixture of at least a redox mediator and an enzyme (GOD or PQQ-GDH), and optionally with one or more of a surfactant, a polymer binder, and a buffer. The reference electrode may be loaded with the same mixture as the working electrode. It should be pointed out that the reference electrode opening could be loaded with a redox mediator (either reduced or oxidized form or the mixture) with or without at least a surfactant, a polymer binder and a buffer. Alternatively, the reference electrode opening could also be loaded with a Ag/AgCl layer (e.g. by applying Ag/AgCl ink or by sputter-coating a silver or silver/silver chloride layer) or other reference electrode materials.

In the second embodiment of the present invention, the glucose sensor has a similar structure to the first embodiment, but it has an additional blank electrode, which is loaded with a mediator and other ingredients without adding glucose sensitive enzyme. Such a four-electrode system not only possesses the feature of the first embodiment, but also the capability of eliminating interference from oxidizable species in the sample such as ascorbic acid, acetaminophen and uric acid etc.

In one aspect of the second embodiment, at least four conductive paths are delineated on the base layer. The reagent holding layer contains at least four openings for three working electrodes and a reference electrode.

In another aspect of the second embodiment, one opening contains electrode material for the first working electrode (W1) loaded with GOD, a mediator and other indigents, one for the second working electrode (W2) loaded with PQQ-GDH, a mediator and other indigents, one for the blank electrode (B) loaded with a mediator and other indigents, and one for the reference electrode (R). The positional arrangement of the working electrodes, blank electrode and the reference electrode in the channel is not critical for obtaining usable results from the electrochemical sensor. The preferred position was found to be W1-W2-R-B; that is, as the sample fluid entered the open end of the laminated body, the fluid would cover W1 first, then W2, then R, then B.

In yet another embodiment of the present invention, the glucose sensor has a similar structure to the first embodiment, but without using the reagent holding layer. The three remaining layers are the same as in the first embodiment. The details of this construction have been disclosed in U.S. Pat. No. 6,258,229. The U-shaped channel cutout is located at the sensor end (sample entrance end). The length, thickness and width of the U-shaped channel cutout define the capillary channel size or volume. The length and width of the U-shaped channel cutout along with the base conductive layer define the areas of the working and reference electrodes and the sample chamber, but, as disclosed above, may have an alternative chemical construction.

In one aspect of the previous embodiment, the working electrodes (W1 and W2) are loaded with at least an enzyme (GOD or PQQ-GDH), a redox mediator, a polymer binder, a surfactant and a buffer. The reference electrode (R) is preferably covered by the same reagent mixture as one of the working electrodes.

In a fourth embodiment of the present invention, the glucose sensor is based on screen-printing technology. The conductive ink (e.g. carbon ink for working electrodes; silver/silver chloride ink for reference electrode) is printed onto a base layer serving as electrodes after drying. The capillary channel can be formed by applying a U-shape spacer and a cover as described in the previous embodiments. The U-shaped channel cutout is located at the sensor end (sample entrance end). The length, thickness and width of the U-shaped channel cutout define the capillary channel size or volume.

In one aspect of the fourth embodiment, the working electrodes (W1 and W2) are loaded with at least an enzyme (GOD or GDH-PQQ), a redox mediator, a polymer binder, a surfactant and a buffer. The reference electrode (R) may or may not be covered by the same reagent mixture as one of the working electrodes.

In another aspect of the fourth embodiment, the enzymes and redox mediator and other ingredients can be mixed with the ink and screen-printed onto the base insulated layer.

In a fifth embodiment of the present invention, the glucose sensor has two channels (channel 1 and channel 2) on the same strip; each channel can have a similar structure to those mentioned in the above embodiments. Channel 1 and channel 2 are arranged side by side or back to back. The sample entrances of the two channels are close to each other; or the two channels simply share the same sample entrance.

In one aspect of the fifth embodiment, Channel 1 has at least one working electrode and one reference electrode. At least one of the working electrodes is loaded with GOD, a mediator and other ingredients. Channel 1 can function independently as one glucose sensor.

In another aspect of the fifth embodiment, Channel 2 has at least one working electrode and one reference electrode. At least one of the working electrodes is loaded with PQQ-GDH, a mediator and other ingredients. Channel 2 can function independently as another glucose sensor independently.

In yet another embodiment of the present invention, the disposable strip has a sensor body with an open well forming a test chamber, at least two working electrodes and a reference electrode within the test chamber, and electrical contacts for electrically connecting the at least two working electrodes and the reference electrode to a meter device. The test chamber contains at least two reagents, one on each of the at least two working electrodes where one of the reagents contains GOD and the other contains GDH. The meter device must be capable of providing a biasing potential across the working electrodes and the reference electrode and detecting a current generated by the presence of glucose in a fluid sample disposed into the open well of the disposable strip.

All of the advantages of the present invention will be made clearer upon review of the detailed description, drawings and appended claims.

BRIEF DESCRIPTION OF THE DRAWINGS

FIG. 1 is a perspective view of one embodiment of the present invention showing the test strip.

FIG. 2 is an exploded view of the embodiment in FIG. 1 showing the four component layers of the test strip.

FIG. 3 is a perspective view of another embodiment of the present invention showing the test strip.

FIG. 4 is an exploded view of the embodiment in FIG. 3 showing the three component layers of the test strip.

FIG. 11 is a perspective view of another embodiment of the present invention showing the combination of a three-layer GOD-based sensor strip and a three-layer GDH-based sensor strip where the base layer is common to both sensors.

FIG. 12 is an exploded view of the embodiment in FIG. 111 showing the arrangement of the component layers of the GOD-based sensor and the GDH-based sensor.

FIG. 13 is a perspective view of another embodiment of the present invention showing a combined sensor strip having the four-layer construction with two working electrodes and a blank electrode, namely, a GOD-based electrode, a GDH-based electrode and an interferant-compensating electrode.

FIG. 14 is an exploded view of the embodiment in FIG. 13 showing the arrangement of the component layers that includes a GOD-based electrode, a GDH-based electrode, an interferent-compensating electrode, and a reference electrode.

FIG. 15 is a perspective view of another embodiment of the present invention showing a combined sensor strip having the four-layer construction with a GOD-based sensor system side-by-side with a GDH-based electrode.

FIG. 16 is an exploded view of the embodiment in FIG. 15 showing the arrangement of the component layers that includes the GOD-based electrode system and the GDH-based electrode system.

FIG. 17 is a perspective view of another embodiment of the present invention showing a combined sensor strip having the three-layer construction with a GOD-based sensor system side-by-side with a GDH-based electrode.

FIG. 18 is an exploded view of the embodiment in FIG. 17 showing the arrangement of the component layers that includes the GOD-based electrode system and the GDH-based electrode system.

DETAILED DESCRIPTION OF THE PREFERRED EMBODIMENT

Figure 5:
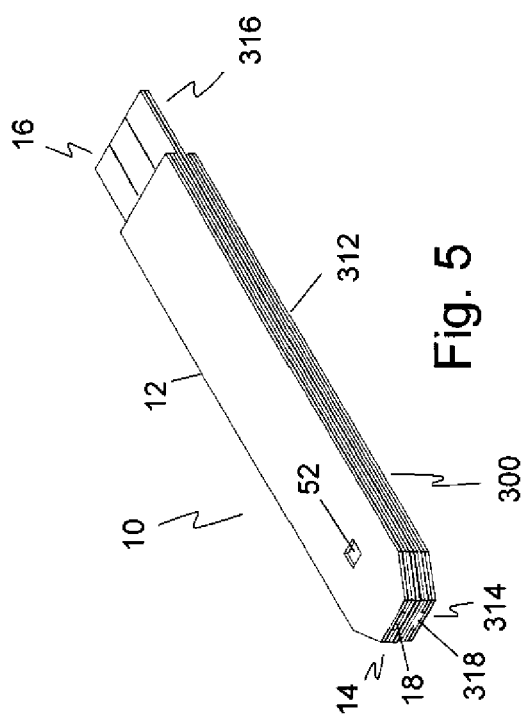
FIG. 5 is a perspective view of another embodiment of the present invention showing the combination of a four-layer GOD-based sensor strip and a four-layer GDH-based sensor strip.

The preferred embodiments of the present invention are illustrated in FIGS. 1-25. The glucose sensor of the present invention can be made using either a 4-layer construction (FIG. 1) or a 3-layer construction (FIG. 3). The 4-layer construction has the same three layers as the 3-layer construction and an additional reagent holding layer between a base/bottom layer and a channel forming layer.

Turning now to FIG. 1, the glucose strip 10 has a laminated body 12, a fluid sampling end 14, an electrical contact end 16, and a vent opening 52. Fluid sampling end 14 includes a sample chamber 17 between a sample inlet 18 and vent opening 52. Electrical contact end 16 has three discrete conductive contacts 16a, 16b and 16c.

Turning now to FIG. 2, laminated body 12 is composed of a base layer 20, a reagent holding layer 30, a channel forming layer 40, and a cover 50. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

Base layer 20 has a conductive layer 21 on which is delineated three conductive paths 22, 24 and 26. The conductive paths 22, 24, 26 may be formed by scribing or scoring conductive layer 21, or by silk-screening conductive paths 22, 24, 26 onto base layer 20. Scribing or scoring of conductive layer 21 may be done by mechanically scribing the conductive layer 21 sufficiently to create the three independent conductive paths 22, 24, 26. The preferred scribing or scoring method of the present invention is done by using a carbon dioxide laser, a YAG laser or an eximer laser. Conductive layer 21 may be made of any electrically conductive material such as, for example, gold, tin oxide/gold, palladium, other noble metals or their oxides, or carbon film compositions. The preferred electrically conductive material is gold or tin oxide/gold. A usable material for base layer 20 is a tin oxide/gold polyester film (Cat. No. FM-1) or a gold polyester film (Cat. No. FM-2) sold by Courtaulds Performance Films, Canoga Park, Calif.

In the embodiments using a reagent holding layer 30 (4-layer construction), reagent holding layer 30 has three reagent holding openings 32, 34 and 36. Reagent holding opening 32 exposes a portion of conductive path 22, reagent holding opening 34 exposes a portion of conductive path 24, and reagent holding opening 36 exposes a portion of conductive path 26 creating reagent holding wells. Reagent holding layer 30 is made of a plastic material, preferably a medical grade one-sided adhesive tape available from Adhesive Research, Inc., of Glen Rock, Pa. Acceptable thicknesses of the tape for use in the present invention are in the range of about 0.001 in. (0.025 mm) to about 0.005 in. (0.13 mm). One such tape, Arcare® 7815 (about 0.0025 in. (0.063 mm)), is preferred due to its ease of handling and good performance in terms of its ability to hold a sufficient quantity of chemical reagents and to promote capillary action through the sample chamber of the sensor. It should be understood that the use of a tape is not required. Reagent holding layer 30 may be made from a plastic sheet and may be coated with a pressure sensitive adhesive, a photopolymer, ultrasonically-bonded to base layer 20, or silk-screened onto the base layer 20 to achieve the same results as using the polyester tape mentioned.

The three reagent holding openings 32, 34, 36 define electrode areas W1, W2 and R, respectively, and hold chemical reagents forming two working electrodes (a GOD-based glucose electrode and a GDH-based glucose electrode) and one reference electrode. Generally, the electrode areas are loaded with the reagent mixtures. The reagent mixtures for the working electrode areas 32, 34, 36 are a mixture of enzymes and redox mediators with optional polymers, surfactants, and buffers. A reference reagent matrix may be loaded in electrode area R that is similar to the reagent mixture of the working electrodes.

Typically, electrode area R must be loaded with a redox reagent or mediator to make the reference electrode function when using the preferred conductive coating material. The reference reagent mixture preferably contains either oxidized or a mixture of an oxidized and reduced form of redox mediators, at least one binder, a surfactant and an antioxidant (if a reduced form of redox mediator is used) and a bulking agent. In the alternative, the reference electrode (electrode area R) could be also loaded with a Ag/AgCl layer (e.g. by applying Ag/AgCl ink or by sputter-coating a Ag or Ag/AgCl layer) or other reference electrode materials that do not require a redox mediator to function properly.

The size of the reagent holding openings is preferred to be made as small as possible in order to make the sample chamber of the glucose sensor as short as possible while still being capable of holding sufficient chemical reagent to function properly. The preferred shape of the reagent holding openings is round and has a preferred diameter of about 0.03 in. (0.76 mm). The three reagent holding openings 32, 34, 36 are aligned with each other and are spaced about 0.025 in. (0.625 mm) from each other. The circular reagent holding openings are for illustrative purposes only and it should be understood that the shape of the reagent holding openings is not critical.

The positional arrangement of the working electrode and the reference electrode in the channel is not critical for obtaining usable results from the glucose sensor. The possible electrode arrangements within the sample fluid channel may be W1-W2-R, W1-R-W2, R-W1-W2, W2-W1-R, W2-R-W1, or R-W2-W1, with the arrangement listed as the electrodes would appear from the sample inlet 18 of laminated body 12 to the vent opening 52. The preferred position was found to be W1-W2-R; that is, as the fluid sample enters sampling end 14 of laminated body 12, the fluid sample would cover W1 first, then W2, then R. Such an arrangement may be beneficial for obtaining usable results when the sample is insufficient or partially insufficient.

The working electrodes and the reference electrode are each in electrical contact with separate conductive paths. The separate conductive paths terminate and are exposed for making an electrical connection to a reading device on the end opposite the sample inlet 18 of laminated body 12.

In the embodiments using reagent holding layer 30 (4-layer construction), channel forming layer 40 has a U-shaped cutout 42 located at the fluid sampling end 14. The length of cutout 42 is such that when channel forming layer 40 is laminated to reagent holding layer 30, electrode areas W and R are within the space defined by cutout 42. The length, width and thickness of the U-shaped cutout 42 define the capillary channel volume. The thickness of channel forming layer 40 can affect the speed of the sample fluid flow into the fluid sample channel, which is filled by capillary action of the sample fluid. Channel forming layer 40 is made of a plastic material, preferably a medical grade double-sided pressure sensitive adhesive tape available from Adhesive Research, Inc., of Glen Rock, Pa. Acceptable thicknesses of the tape for use in the present invention are in the range of about 0.001 in. (0.025 mm) to about 0.010 in. (0.25 mm). One such tape is Arcare® 7840 (about 0.0035 in. (0.089 mm)). U-shaped cutout 42 can be made with a laser or by die-cutting. The preferred method is to die-cut the cutout. The preferred size of the U-shaped cutout is about 0.05 in. wide (1.27 mm) and about 0.0035 in. thick (0.089 mm). The length is dependent on the number of the layer 2 openings.

Cover 50, which is laminated to channel forming layer 40, has vent opening 52 spaced from the fluid sampling end 14 of glucose sensor 10 to insure that fluid sample in the sample chamber 17 will completely cover electrode areas W1, W2 and R. Vent opening 52 is positioned in cover 50 so that it will align somewhat with U-shaped cutout 42. Preferably, vent opening 52 will expose a portion of and partially overlay the base of the U-shaped cutout 42. The preferable shape of vent hole 52 is a rectangle with dimensions of about 0.08 in. (2 mm) by about 0.035 in. (0.9 mm). Preferably, the top layer also has a notch 54 at fluid sampling end 14 to facilitate loading of the fluid sample into sample chamber 17. The preferred shape is a half circle, which is located approximately in the middle of the channel entrance. The preferred size is 0.028 in. (0.71 mm) in diameter. The preferred material for cover 50 is a polyester film. In order to facilitate the capillary action, it is desirable for the polyester film to have a highly hydrophilic surface that faces the capillary channel. Transparency films (Cat. No. PP2200 or PP2500) from 3M are the preferred material used as the cover in the present invention.

FIG. 3 illustrates a 3-layer glucose sensor 10'. Like the 4-layer embodiment, glucose sensor 10' has a laminated body 12, a fluid sampling end 14, an electrical contact end 16, and a vent opening 52. Fluid sampling end 14 includes a sample chamber 17 between a sample inlet 18 and vent opening 52. Electrical contact end 16 has three discrete conductive contacts 16a, 16b and 16c.

As can be seen from FIG. 4, laminated body 12 is composed of a base layer 20, a channel forming layer 40, and a cover 50. As noted earlier, all layers of laminated body 12 are made of a dielectric material, preferably plastic. Unlike the 4-layer embodiment, there is no separate reagent holding layer in the 3-layer embodiment. Channel forming layer 40 also delineates the area in which a pre-determined amount of reagent mixtures are disposed onto the conductive paths as three distinct drops or droplets on the two working electrodes and the reference electrode, respectively.

FIG. 5 shows a combination of a GOD-based glucose sensor 10 and a GDH-based glucose sensor 300. Both GOD-based glucose sensor 10 and GDH-based glucose sensor 300 are made of the 4-layer construction where the base layers of each sensor are laminated to each other forming an integrated glucose sensor combination. Each sensor has a laminated body 12, 312, a fluid sampling end 14, 314, an electrical contact end 16, 316, and a vent opening 52, 352 (not shown). Fluid sampling ends 14, 314 include sample chambers (not shown) between sample inlets 18, 318 and vent openings 52, 352, respectively.

Figure 6:
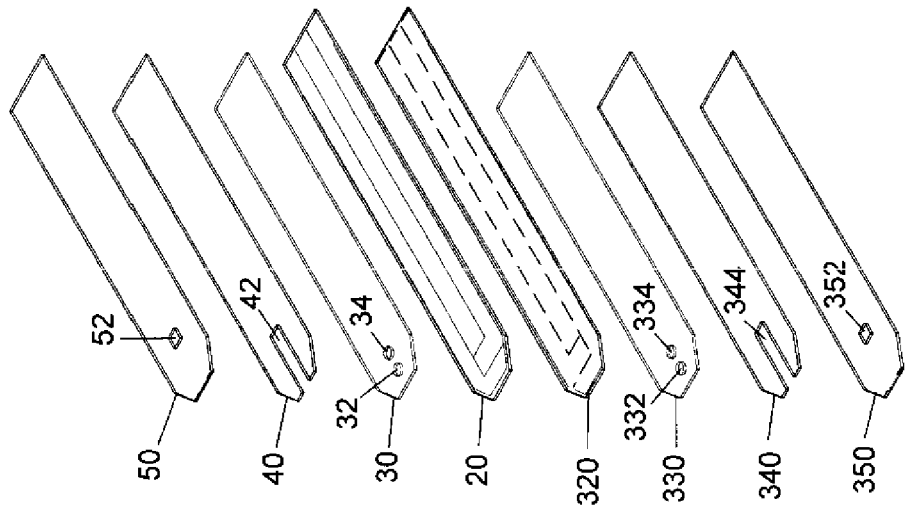
FIG. 6 is an exploded view of the embodiment in FIG. 5 showing the arrangement of the component layers of the GOD-based sensor strip and the GDH-based sensor strip.

Turning now to FIG. 6, each sensor 10, 300 has a base layer 20, 320, a reagent holding layer 30, 330, a channel forming layer 40, 340, and a cover 50, 350. Reagent holding layers 30, 330 have reagent holding openings 32, 34 and 332, 334, respectively. Channel forming layers 40, 340 have U-shaped cutouts 42, 342, respectively. Typically, an adhesive is used to hold sensors 10 and 300 together. Preferably, an additional layer (not shown) with adhesive on both sides is used to facilitate assembly of sensor 10 to sensor 300.

Figure 7:
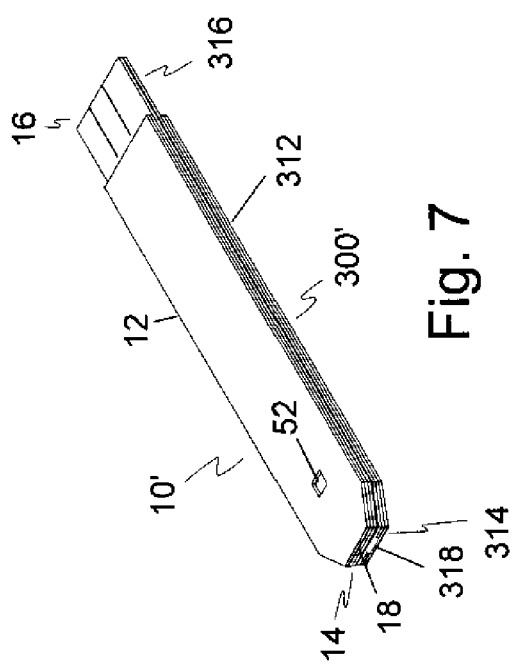
FIG. 7 is a perspective view of another embodiment of the present invention showing the combination of a three-layer GOD-based sensor strip and a three-layer GDH-based sensor strip.

FIG. 7 shows another combination embodiment of a GOD-based glucose sensor 10' and a GDH-based glucose sensor 300'. Both GOD-based glucose sensor 10' and GDH glucose sensor 300' are made of the 3-layer construction where the bases of each sensor are laminated to each other forming an integrated combination. Each sensor has a laminated body 12, 312, a fluid sampling end 14, 314, an electrical contact end 16, 316, and a vent opening 52, 352 (not shown). Fluid sampling ends 14, 314 include sample chambers (not shown) between sample inlets 18, 318 and vent openings 52, 352, respectively.

Figure 8:
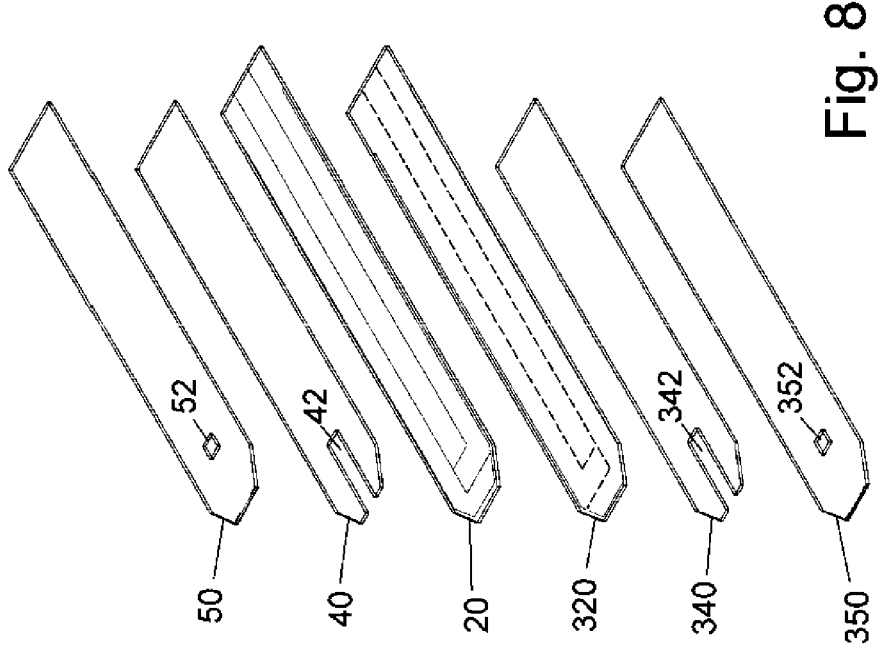
FIG. 8 is an exploded view of the embodiment in FIG. 7 showing the arrangement of the component layers of the GOD-based sensor strip and the GDH-based sensor strip.

Turning now to FIG. 8, each sensor 10', 300' has a base layer 20, 320, a channel forming layer 40, 340, and a cover 50, 350. Channel forming layers 40, 340 have U-shaped cutouts 42, 342, respectively.

Figures 9, 10:
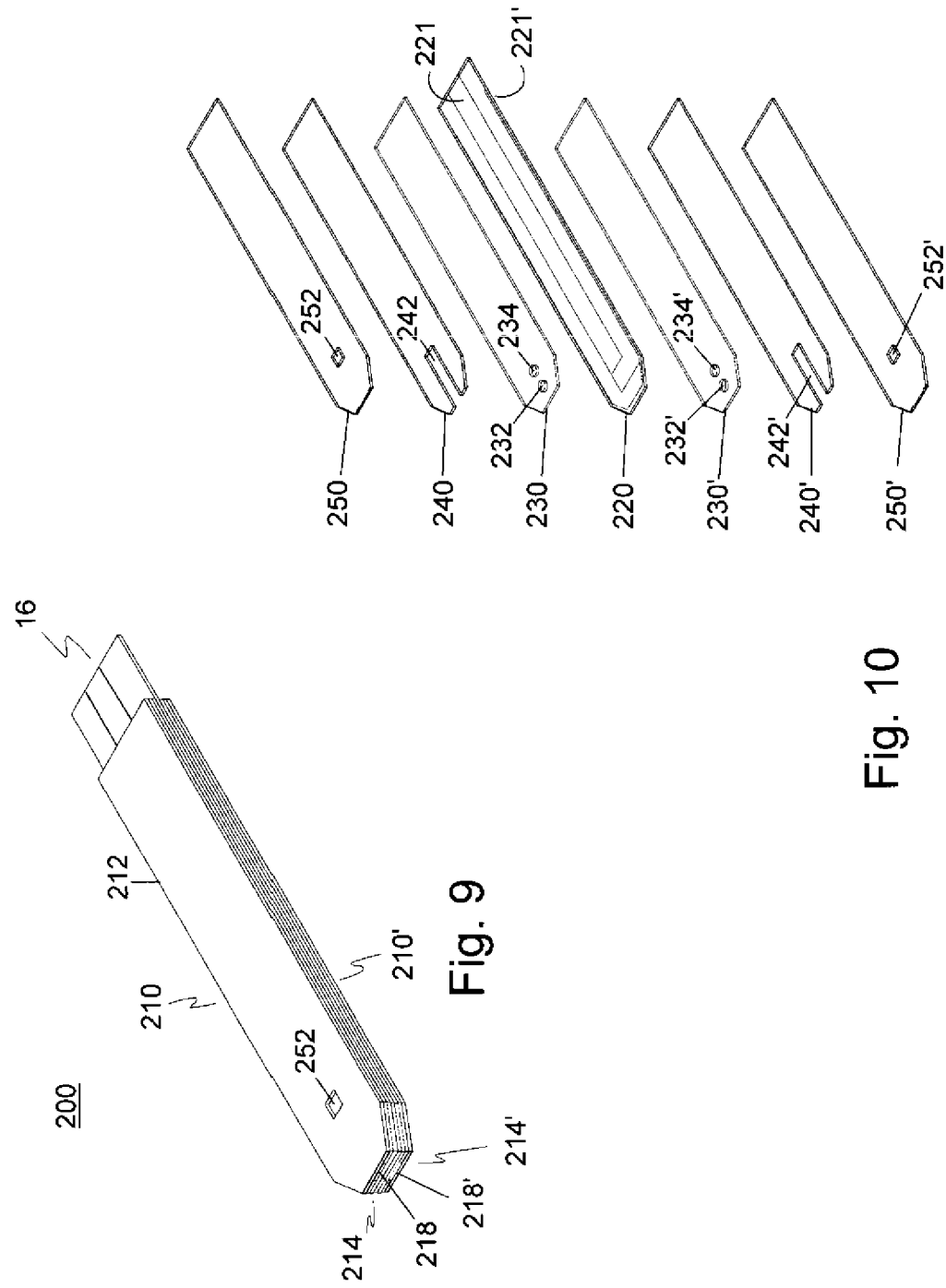
FIG. 9 is a perspective view of another embodiment of the present invention showing the combination of a four-layer GOD-based sensor strip and a four-layer GDH-based sensor strip where the base layer is common to both sensors.
FIG. 10 is an exploded view of the embodiment in FIG. 9 showing the arrangement of the component layers of the GOD-based sensor and the GDH-based sensor.

FIG. 9 illustrates a GOD-based glucose sensor and a GDH-based glucose sensor combination 200 with a 7-layer laminated body 212. The combination includes a GOD-based glucose sensor 210 and a GDH-based glucose sensor 210'. Laminated body 212 includes a fluid sampling end 214, an electrical contact end 216 and vent openings 252, 252' (not shown). Fluid sampling end 14 includes two sample fluid channels (not shown); one between sample inlet 218 and vent opening 252 and the other between sample inlet 218' and vent opening 252' (not shown).

FIG. 10 shows an expanded view of laminated body 212 of the embodiment in FIG. 9. Laminated body 212 has a central, base layer 220 with a conductive coating 221, 221' on each side delineating the conductive paths for the working and reference electrodes of each sensor. Each side of central, base layer 220 includes a reagent holding layer 230, 230', a channel forming layer 240, 240', and a cover 250, 250'. Reagent holding layers 230, 230' have reagent holding openings 232, 234 and 232', 234', respectively. Channel forming layers 240, 240' have U-shaped cutouts 242, 242', respectively.

FIG. 11 illustrates a GOD-based glucose sensor and a GDH-based glucose sensor combination 400 with a 5-layer laminated body 412. The combination 400 includes a GOD-based glucose sensor 410 and a GDH-based glucose sensor 410'. Laminated body 412 includes a fluid sampling end 414, an electrical contact end 416 and vent openings 452, 452' (not shown). Fluid sampling end 414 includes two sample chambers (not shown); one between sample inlet 418 and vent opening 452 and the other between sample inlet 418' and vent opening 452' (not shown).

FIG. 12 shows an expanded view of laminated body 412 of the embodiment in FIG. 11. Laminated body 412 has a central, base layer 420 with a conductive coating 421, 421' on each side delineating the conductive paths for the working and reference electrodes of each sensor. Each side of central, base layer 420 includes a channel forming layer 440, 440' and a cover 450, 450'. Channel forming layers 440, 440' have U-shaped cutouts 442, 442', respectively.

It should be noted that, in any of the combination sensor systems, the inlet notch may be incorporated into the base layers and the reagent holding layers to facilitate loading of a portion of the fluid sample in each of the sample chambers of the GOD-based and the GDH-based glucose sensors.

FIG. 13 illustrates yet another embodiment of the present invention showing a combination GOD-based and a GDH-based glucose sensor with intereferant correction. FIG. 13 shows a combination GOD-based and a GDH-based glucose sensor 600 with a laminated body 612, a fluid sampling end 614, an electrical contact end 616 and a vent opening 652. Sensor 600 may also include an optional inlet notch 654. Fluid sampling end 614 includes a fluid sample chamber 617 between sample inlet 618 and vent opening 652.

FIG. 14 shows an expanded view of laminated body 612 of the embodiment in FIG. 13. Laminated body 612 has a base layer 620, a reagent holding layer 630, a channel forming layer 640 with a U-shaped cutout 642, and a cover 650 with an optional inlet notch 654. Base layer 620 has a conductive layer 621 on which is delineated at least four conductive paths 622, 624, 626, and 628. Reagent holding layer 630 has at least four reagent holding openings 632, 634, 636, and 638. Reagent holding opening 632 exposes a portion of conductive path 622, reagent holding opening 634 exposes a portion of conductive path 624, reagent holding opening 636 exposes a portion of conductive path 626, and reagent holding opening 638 exposes a portion of conductive path 628; all forming respective electrode wells.

The four reagent holding openings 632, 634, 636, and 638 define electrode areas W1, W2, R, and B, respectively, and hold chemical reagents forming a first working electrode, a second working electrode, one reference electrode, and a blank electrode. Generally, electrode area W1 is loaded with a GOD-based reagent that includes a glucose oxidase and a redox mediator (preferably an oxidized form of the redox mediator). Electrode area W2 is loaded with a GDH-based reagent that includes PQQ-GDH and a redox mediator (preferably an oxidized form of the redox mediator). A reference reagent matrix may be loaded in both electrode area B and electrode area R that is similar to the GOD-based reagent mixture or the GDH-based reagent mixture without the glucose-based enzymes.

Typically, electrode area R must be loaded with a reference reagent such as, for example, a redox couple/a redox reagent. Electrode area R may, in the alternative, be loaded with a Ag/AgCl layer (e.g. by applying Ag/AgCl ink or by sputter-coating a Ag or Ag/AgCl layer) or other reference electrode materials. Electrode area B may be loaded with any reagent mixture without an addition of glucose-based enzyme.

In addition to measuring the fluid sample resistance between electrode area B and the reference electrode to compensate the sensor readings for blood hematocrit, oxidizable interferants such as ascorbic acid, uric acid and acetaminophen, to name a few, (which also cause inaccurate readings in the output of the electrochemical biosensor), can also be measured to compensate the sensor readings for these interferants. The interferant effect can be negated by subtracting the current response at B (blank electrode) from the current response from W2 (second working electrode) as well as W1 (first working electrode) to calculate the concentration in the sample fluid. This is achieved by maintaining the surface area ratio of B to W2 and B to W1 constant.

Turning now to FIG. 15, there is illustrated a 4-layer configuration of another embodiment of the present invention showing a combination of a GOD-based sensor system and a GDH-based sensor system in a side-by-side configuration. FIG. 15 shows a combination GOD-based and a GDH-based glucose sensor 700 with a laminated body 712, a fluid sampling end 714, an electrical contact end 716 and a vent opening 752. Sensor 700 may also include an optional inlet notch 754. Fluid sampling end 714 includes a first sample chamber 717*a* and a second sample chamber 717*b* between sample inlet 718 and vent opening 752. It should be understood that sample inlet 718 may optionally be two inlets (one for each of the fluid sample channels) adjacent each other and that vent opening 752 may also optionally incorporate separate vent openings for each of the fluid sample channels. In the illustrated embodiment, one of the sample chambers incorporates the GOD-based sensor system and the other sample chamber incorporates the GDH-based sensor system.

FIG. 16 shows an expanded view of laminated body 712 of the embodiment in FIG. 15. Laminated body 712 has a base layer 720, a reagent holding layer 730, a channel forming layer 740 with a fork-shaped cutout 742 having a first leg 742a and a second leg 742b that form sample chambers 717a, 717b, respectively, and a cover 750 with an optional inlet notch 754. Base layer 720 has a conductive layer 721 on which is delineated at least four conductive paths 722, 724, 728, and 729. Conductive layer 721 may also include additional conductive paths 726, 727 to provide interferant and/or hematocrit compensating electrodes.

Reagent holding layer 730 has at least four reagent holding openings 732, 734, 738, and 739. Reagent holding opening 732 exposes a portion of conductive path 722, reagent holding opening 734 exposes a portion of conductive path 724, reagent holding opening 738 exposes a portion of conductive path 728, and reagent holding opening 739 exposes a portion of conductive path 729; all forming respective electrode reagent wells.

To include interferant and/or hematocrit compensation, reagent holding layer 730 would include additional reagent holding openings that would expose portions of other conductive paths such as, for example, conductive paths 726 and 727.

FIG. 17 illustrates a 3-layer configuration of another embodiment of the present invention showing a combination of a GOD-based sensor system and a GDH-based sensor system in a side-by-side configuration. FIG. 17 shows a combination GOD-based and a GDH-based glucose sensor 800 with a laminated body 812, a fluid sampling end 814, an electrical contact end 816 and a vent opening 852. Sensor 800 may also include an optional inlet notch 854. Fluid sampling end 814 includes a first sample chamber 817a and a second sample chamber 817b between sample inlet 818 and vent opening 852. Like the 4-layer embodiment previously described, it should be understood that sample inlet 818 may optionally be two inlets (one for each of the sample chambers) adjacent each other and that vent opening 852 may also optionally incorporate separate vent openings for each of the sample chambers. In the illustrated embodiment, one of the sample chambers incorporates the GOD-based sensor system and the other sample chamber incorporates the GDH-based sensor system.

FIG. 18 shows an expanded view of laminated body 812 of the embodiment in FIG. 17. Laminated body 812 has a base layer 820, a channel forming layer 840 with a fork-shaped cutout 842 having a first leg 842a and a second leg 842b that form fluid sample channels 817a, 817b, respectively, and a cover 850 with an optional inlet notch 854. Base layer 820 has a conductive layer 821 on which is delineated at least four conductive paths 822, 824, 828, and 829. Conductive layer 821 may also include additional conductive paths 826, 827 to provide additional electrode systems.

Figure 19:
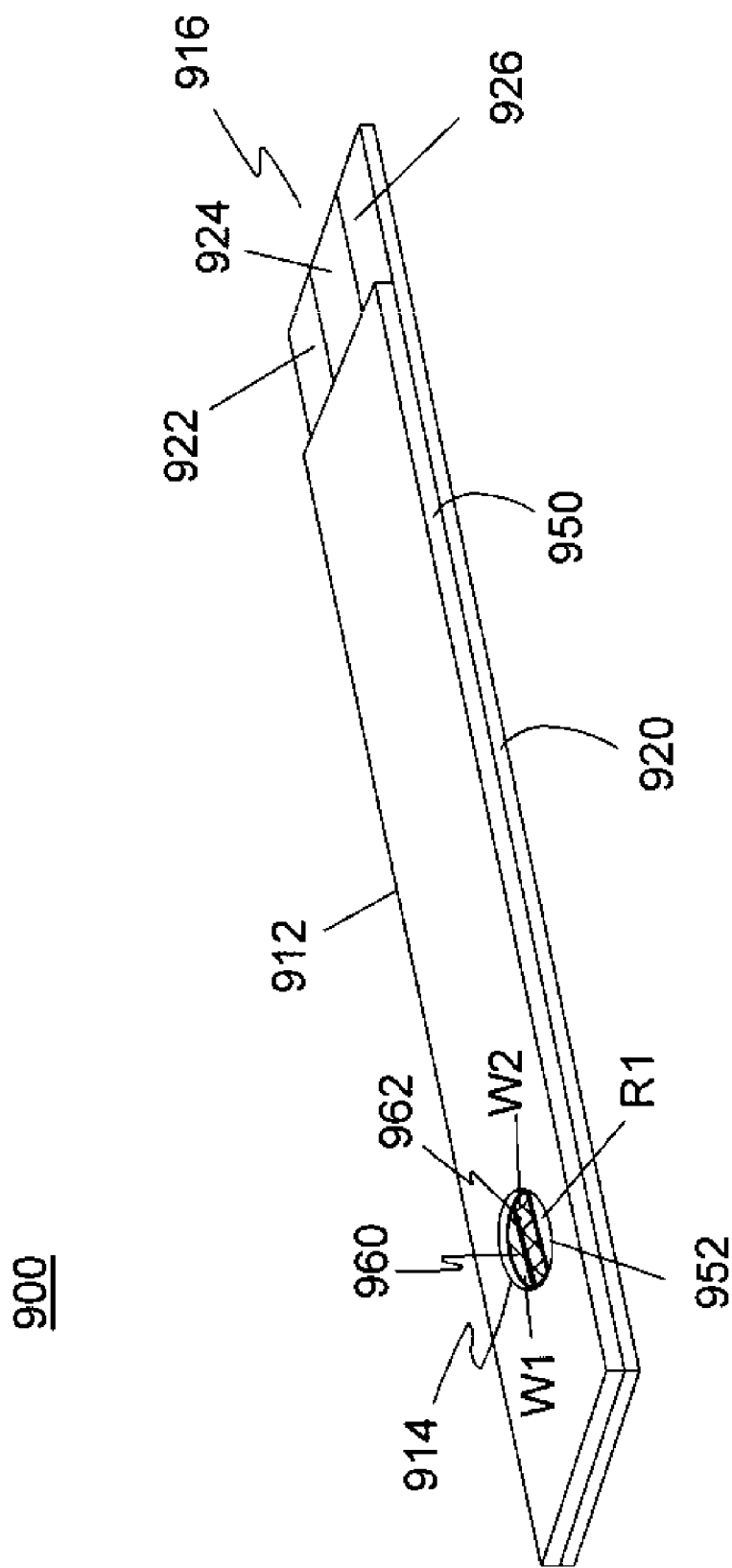
FIG. 19 illustrates a perspective view of another embodiment of the present invention.

Turning now to FIG. 19, there is illustrated another embodiment of the present invention showing a basic disposable glucose sensor 900. Disposable sensor 900 has a laminated body 912, a sample receiving well 914 and an electrical contact end 916. Laminated body 912 has a base layer 920 and a cover 950. Cover 950 has a sample opening 952 that forms, when combined with base layer 920, sample receiving well 914. Base layer 920 has at least three electrical paths 922, 924 and 926, which have a first portion exposed at electrical contact end 916 for connection to a meter device (not shown) and a second portion exposed by sample receiving well 914.

The second portion of electrical paths 922, 924 and 926 exposed by sample receiving well 914 create at least a first working electrode W1, a second working electrode W2 and at least a reference/counter electrode R1. A partition is preferred in order to separate W1 and W2. A first reagent mixture 960 contains at least glucose oxidase and is disposed on the first working electrode W1. A second reagent mixture 962 contains at least glucose dehydrogenase and is disposed on the second working electrode W2. The reference/counter electrode R1 may contain any reference material previously disclosed. In this embodiment of the present invention, sample receiving well 914 serves as both the sample inlet and the sample chamber for receiving a fluid sample such as blood for the determination of glucose.

It should be understood that the conduit paths in any of the embodiments disclosed herein may be made from any non-corroding metal. Carbon deposits such as for example carbon paste or carbon ink may also be used as the conduit paths, all as is well known by those of ordinary skill in the art.

Enzymes

The glucose strip of the present invention includes at least two glucose-sensitive enzymes capable of oxidizing glucose. One is glucose oxidase that does not react with other sugars like maltose and galactose. The second one is oxygen-insensitive glucose dehydrogenase. In the present invention, glucose oxidase is added into the reagent mixture 1 (disclosed below) used for the first working electrode. In the present invention, PQQ dependent glucose dehydrogenase (PQQ-GDH) is added into the reagent mixture 2 (disclosed below) used for the second working electrode.

Redox Mediators

Redox mediators are included in the glucose sensor of the present invention. The preferred redox mediators include those capable of oxidizing the reduced form of the enzymes that are capable of selectively oxidizing glucose. It is desirable that the reduced form of the mediator is capable of being oxidized electrochemically at the working electrodes at the applied potential. It is further desirable that the mediator is stable in the matrix. It is still desirable that the mediator can make the reference function properly. The mediator can be selected from, but not limited to, various metal complexes and organic redox compounds. Examples of acceptable redox mediators are potassium ferricyanide, ferrocene and its derivatives, promazine, tetrathiafulvalene, methyl blue, 1,4-benzoquinone, 1,4-bis(N,N-dimethylamino) benzene, 4,4'-dihydrobiphenyl. The preferred mediator in the present invention is potassium ferricyanide ($K_3Fe(CN)_6$). The concentration of potassium ferricyanide in the reagent mixture is preferably 1% (W/W) to 15%.

Polymers

The polymers used as optional binders should be sufficiently water-soluble and should also be capable of stabilizing and binding all other chemicals in the reagents in electrode areas (working electrodes, blank electrode and reference electrode) (when reference electrode is a redox mediator-based reference electrode) to the conductive surface layer. Preferably, two polymers were added in the reagent mixture of the present invention. One of the preferred polymers is polyethylene oxide (PEO). Its molecular weight ranges from thousands to millions. Preferably, the molecular weight is over 1 million. More preferably, the molecular weight is about 4 million. Such a product is available from Scientific Polymer Products, NY, USA (MW 4,000,000, Cat No. 344). The concentration of PEO in the reagent mixture is preferably 0.04% (W/W) to 2%. The second polymer is preferably methylcellulose, which is available under the brand name of Methocel 60 HG (Cat. No. 64655, Fluka Chemicals, Milwaukee, Wis., USA). The concentration of Methocel 60 HG in the reagent mixture is preferably 0.05% (W/W) to 5%.

Surfactants

A surfactant is needed only to facilitate dispensing of the reagent mixture into the openings for the working electrodes, blank electrode and reference electrode as well as for quickly dissolving the dry chemical reagents when a sample is applied to the sample chamber. The amount and type of surfactant is selected to assure the previously mentioned function and to avoid a denaturing effect on the enzymes. Surfactants can be selected from, but are not limited to, various anionic, cationic, non-ionic and zwitterionic detergents, such as a polyoxyethylene ether, Tween 20, sodium cholate hydrate, hexadecylpyridinium cholide monohydrate, CHAPs. The preferred surfactant is a polyoxyethylene ether. More preferably, it is t-octylphenoxypolyethoxyethanol and is available under the brand name Triton X-100. The concentration of Triton X-100 in the reagent mixture is preferably 0.01% (W/W) to 2%.

The Buffer

Optionally, a buffer may be present along with a redox mediator in dried form in the sensor strip of the present invention. The buffer is present in a sufficient amount so as to substantially maintain the pH of the reagent mixtures. Examples of suitable buffers include citric acid, phosphates, carbonates and the like. In the present invention, 20 mM citrate buffer with a pH of about 6 is employed to prepare the reagent mixtures.

Accordingly, the reagent mixture 1 contains 0.75% (W/W) Methocel 60 HG, 0.4% (W/W) polyethylene oxide, 0.4% (W/W) Triton X-100, 8% (W/W) potassium ferricyanide, 1.5% (W/W) glucose oxidase and 20 mM citrate buffer (pH 6). The reagent mixture 2 contains 0.75% (W/W) Methocel 60 HG, 0.4% (W/W) polyethylene oxide, 0.4% (W/W) Triton X-100, 8% (W/W) potassium ferricyanide, 0.2% (W/W) glucose dehydrogense-PQQ and 20 mM citrate buffer (pH 6).

The reagent mixture 1 is used for the first working electrode (W1) and the reagent mixture 2 is used for the second working electrode. For simplicity, the reagent mixture 2 is also used for the reference electrode (for example, 3-electrode system as discussed in the first embodiment of the present invention). For the 4-electrode system which includes a blank electrode, an additional reagent mixture is needed. This additional reagent mixture has a similar composition to the reagent mixtures 1 and 2, but without adding any glucose-sensitive enzyme.

To illustrate the procedures of how to make and test glucose strips of the present invention, the 3-electrode system (the first embodiment) is taken as the example if not stated otherwise.

Preparation of the Reagent Mixtures

Reagent mixture 1 was prepared in two steps:

Step 1: Into 100 ml of 20 mM citrate buffer (pH 6), add 0.75 g Methocel 60 HG, 0.4 g polyethylene oxide, 0.4 g Triton X-100. Stir the solution until dissolved.

Step 2: Into the above solution, add 8 g potassium ferricyanide, 1.5 g glucose oxidase. Stir the solution until dissolved. The resulting solution is ready for dispensing.

Reagent mixture 2 was prepared also in two steps:

Step 1: Into 100 ml of 20 mM citrate buffer (pH 6), add 0.75 g Methocel 60 HG, 0.4 g polyethylene oxide, 0.4 g Triton X-100. Stir the solution until dissolved.

Step 2: Into the above solution, add 8 g potassium ferricyanide, 0.2 g glucose dehydrogenase-PQQ. Stir the solution until dissolved. The resulting solution is ready for dispensing.

Making of the Glucose Sensor

Assembly of the various embodiments of the present invention is relatively straightforward. Generally for the 4-layer configuration, the base layer and reagent holding layer are laminated to each other followed by dispensing the appropriate reagent mixture into each of the reagent holding openings. After drying the reagent mixture, the channel forming layer is laminated onto the reagent holding layer and the cover is then laminated onto the channel forming layer. For the 3-layer construction, the base layer and the channel forming layer are laminated to each other followed by dispensing the appropriate reagent mixture as distinct drops/droplets into the U-shaped channel (or within each of the legs of the fork-shaped cutout of the side-by-side embodiment) onto their respective conductive surface areas. After drying the reagent mixture, the cover is then laminated onto the channel forming layer.

More particularly, a piece of a gold polyester film is cut to shape as illustrated in FIG. 2, forming base layer 20 of sensor 10. A laser (previously disclosed) is used to score the gold polyester film. As illustrated in FIG. 2, the film is scored by the laser such that three electrodes at sample fluid end 14 and three contact points 22, 24 and 26 are formed at electrical contact end 16. The scoring line is very thin but sufficient to create three separate electrical paths. A scoring line 28 may optionally be made, but is not necessary, along the outer edge of base layer 20 to avoid potential static problems which could cause a noisy signal from the finished sensor 10.

A piece of one-sided adhesive tape is then cut to size and shape, forming reagent holding layer 30 so that it will cover a major portion of conductive layer 21 of base layer 20 except for exposing a small electrical contact area illustrated in FIG. 1.

Before attaching reagent holding layer 30 to base layer 20, three circular openings 32, 34 and 36 of substantially equal size are punched by laser, or by mechanical means such as a die-punch assembly, creating electrode openings 32, 34 and 36 in reagent holding layer 30. The preferred hole size for opening 32, 34 and 36 has a typical diameter of about 0.030 in. (0.76 mm). As illustrated in FIG. 2, electrode openings 32, 34 and 36 are aligned with each other and have a spacing of about 0.025 in (0.63 mm) between them. The circular openings are for illustrative purposes only. It should be understood that the shape of the openings is not critical, provided that the size of the openings is big enough to hold sufficient chemical reagents for the electrodes to function properly but small enough to allow for a reasonably small sample chamber. As stated previously, the preferred arrangement of the electrodes formed in openings 32, 34 and 36 is W1 (working electrode 1), W2 (working electrode 2) and R (reference electrode). Reagent holding layer 30 is then attached to base layer 20 in such a way as to define the electrode wells W1, W2 and R. Approximately 0.05 to 0.09 μL of reagent mixture 1 is dispensed into electrode area W1. As described above, reagent mixture 1 is preferably a mixture of an enzyme, a stabilizer, a binder, a surfactant, and a buffer. Similarly, approximately 0.05 to 0.09 μL of reagent mixture 2 is dispersed into electrode areas of W2 and R.

After the addition of the reagents, the reagents are dried. Drying of the reagents can occur within a temperature range of about room temperature to about 80° C. The length of time required to dry the reagents is dependent on the temperature at which the drying process is performed.

After drying, a piece of double-sided tape available from Adhesive Research is fashioned into channel forming layer 40 containing U-shaped channel 42. Channel forming layer 40 is then layered onto reagent holding layer 30. As mentioned earlier, channel forming layer 40 serves as a spacer and defines the size of the sample chamber 17. Its width and length are optimized to provide for a relatively quick moving fluid sample.

A piece of a transparency film (Cat. No. PP2200 or PP2500 available from 3M) is fashioned into top layer/cover 50. A rectangular vent opening 52 is made using the laser previously mentioned or by means of a die-punch. Vent opening 52 is located approximately 0.180 in. (4.57 mm) from sample inlet 18. Cover 50 is aligned and layered onto channel forming layer 40 to complete the assembly of sensor 10, as illustrated in FIG. 1.

Testing of the Glucose Sensor

When a fluid sample is applied to a single strip of the present invention, the fluid sample enters the channel through the sampling end aperture and flows over W1, W2 and R and stops at the threshold of the vent opening.

Chronoamperometry (i-t curve) was used for measurement of the current response of the glucose strips using an Electrochemical Analyzer (Model 812, CH Instruments, Austin, Tex., USA). Oxygen concentration ($pO_2$) was controlled using a Tonometer (Precision Gas Mixer, PGM-3, Medicor, Inc., Salt Lake City, Utah, USA). Once a blood sample enters the strip, a potential of 0.3-0.5 volts is applied across the working electrodes and the reference electrode. The glucose concentration of the same blood sample is measured with a YSI Glucose Analyzer (Model 2300 Stat Plus, YSI Inc., Yellow Spring, Ohio, USA).

The above described embodiments are based on amperometric analyses. Those skilled in the art, however, will recognize that a sensor of the invention may also utilize coulometric, potentiometric, voltammetric, and other electrochemical techniques to determine the concentration of an analyte in a sample.

The following examples illustrate the unique features of the present invention.

EXAMPLE 1

Demonstration of Current Response at Different Levels of $pO_2$

Blood samples with different $pO_2$ levels and different glucose concentrations were tested with the glucose strips of the present invention in connection with an Electrochemical Analyzer (CH Instruments, Model 812, Austin, Tex., USA). It has been found that the current responses at the first working electrode (i.e. GOD-based electrode) increase with decreasing oxygen concentration in the blood samples or decrease with increasing oxygen concentration in the blood samples. In order to illustrate such an oxygen effect, blood samples with three oxygen levels, i.e. 30, 90, 220 mmHg, were tested.

Figure 20:
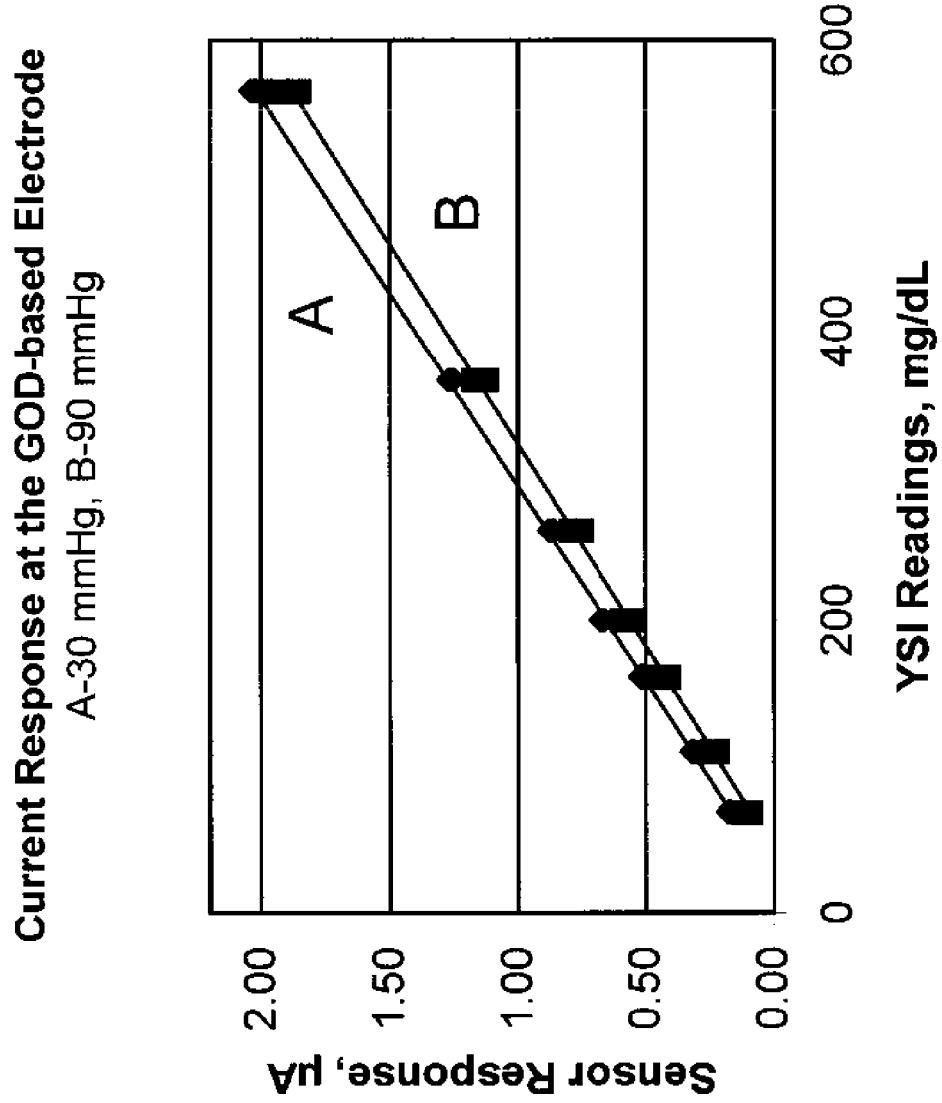
FIGS. 20 and 21 illustrate the correlation between the current response of the GOD-based electrode at different oxygen levels.

FIG. 20 shows the measured current response of the first working electrode (i.e. GOD-based electrode) to varying glucose concentrations at $pO_2$ levels of 30 and 90 mmHg. The current responses are linear to the glucose concentration throughout the glucose concentration range tested for the two levels of oxygen. However, as expected, the current response at $pO_2$ level of 30 mmHg is significantly higher than those at $pO_2$ level of 90 mmHg. Upon converting the change in current response to glucose concentration, the average difference in glucose concentration at the GOD-based working electrode is about 24.3 mg/dL for the $pO_2$ level change from 30 to 90 mmHg.

Figure 21:
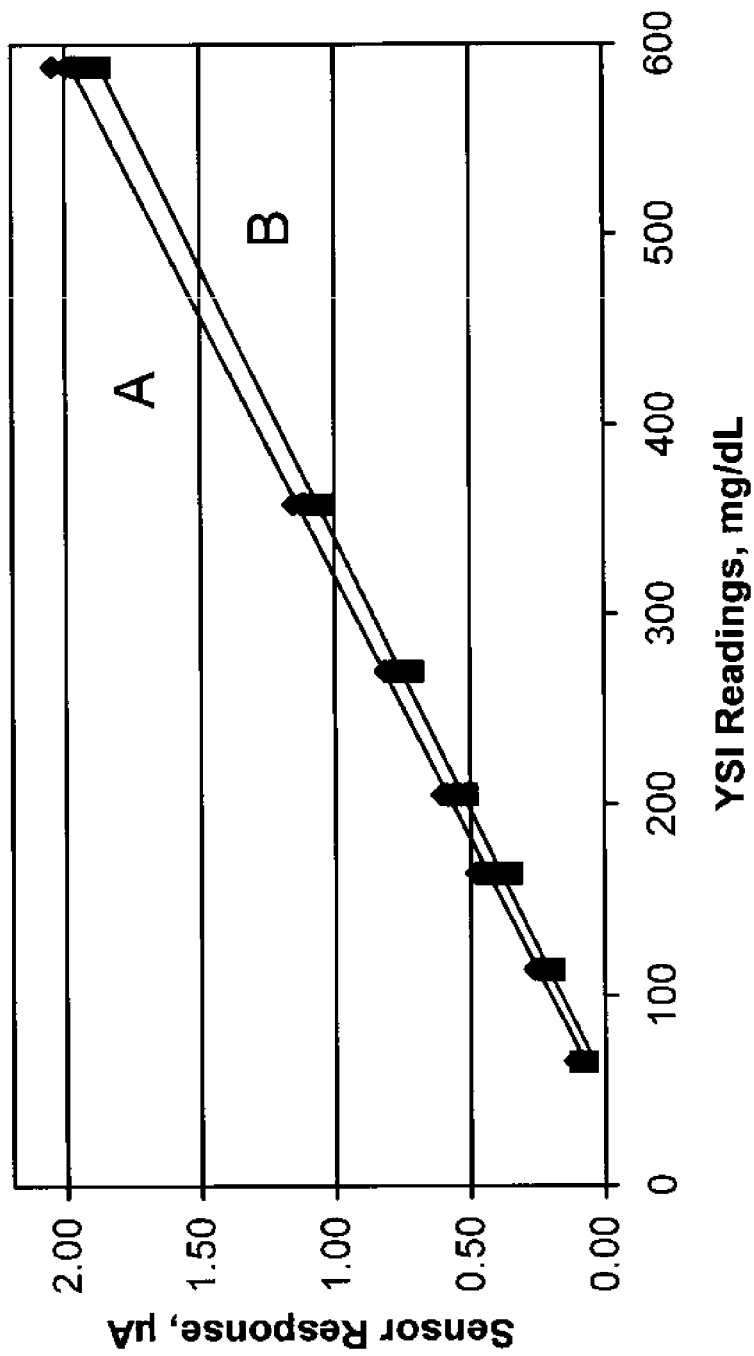

FIG. 21 shows the measured current response of the GOD-based electrode to varying concentrations at $pO_2$ levels of 90 and 220 mmHg. The current responses are linear to the glucose concentration throughout the glucose concentration range tested for the oxygen level of 220 mmHg. However, as expected, the current response at $pO_2$ level of 220 mmHg is significantly lower than those at $pO_2$ level of 90 mmHg. Upon converting the change in current response to glucose concentration, the average change in glucose concentration at the GOD-based working electrode is about 15.0 mg/dL for the $pO_2$ level change from 90 to 220 mmHg.

Figure 22:
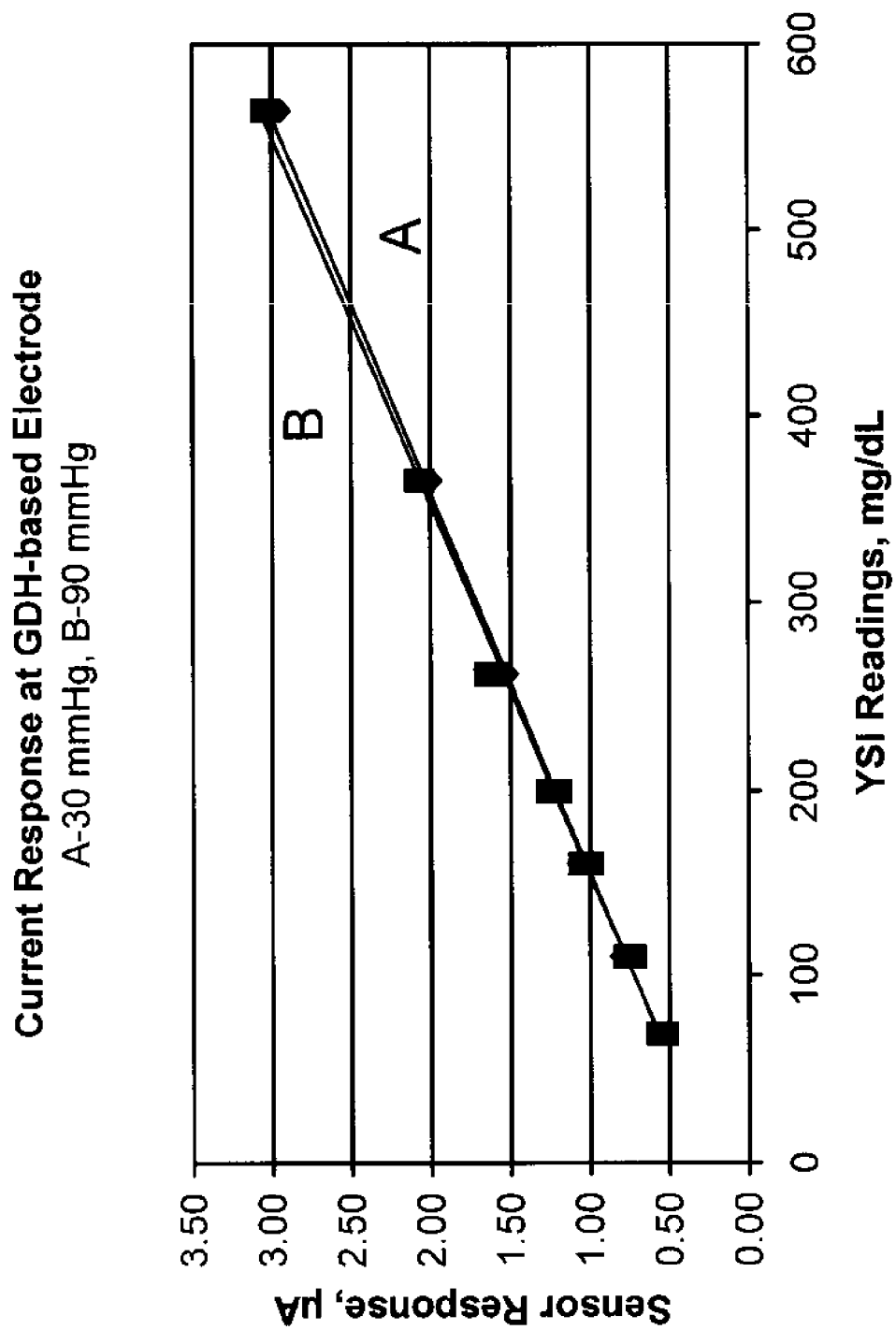
FIGS. 22 and 23 illustrate the correlation between the current response of the GDH-based electrode at different oxygen levels.

FIG. 22 shows the measured current response of the second working electrode (i.e. GDH-based electrode) to varying glucose concentrations at $pO_2$ levels of 30 and 90 mmHg. The current responses are also linear to the glucose concentration throughout the glucose concentration range tested for the two levels of oxygen. As expected, there is substantially no difference between the current responses at $pO_2$ level of 30 mmHg and at $pO_2$ level of 90 mmHg throughout the glucose concentration range tested because of the inherent character of the GDH-based electrode.

Figure 23:
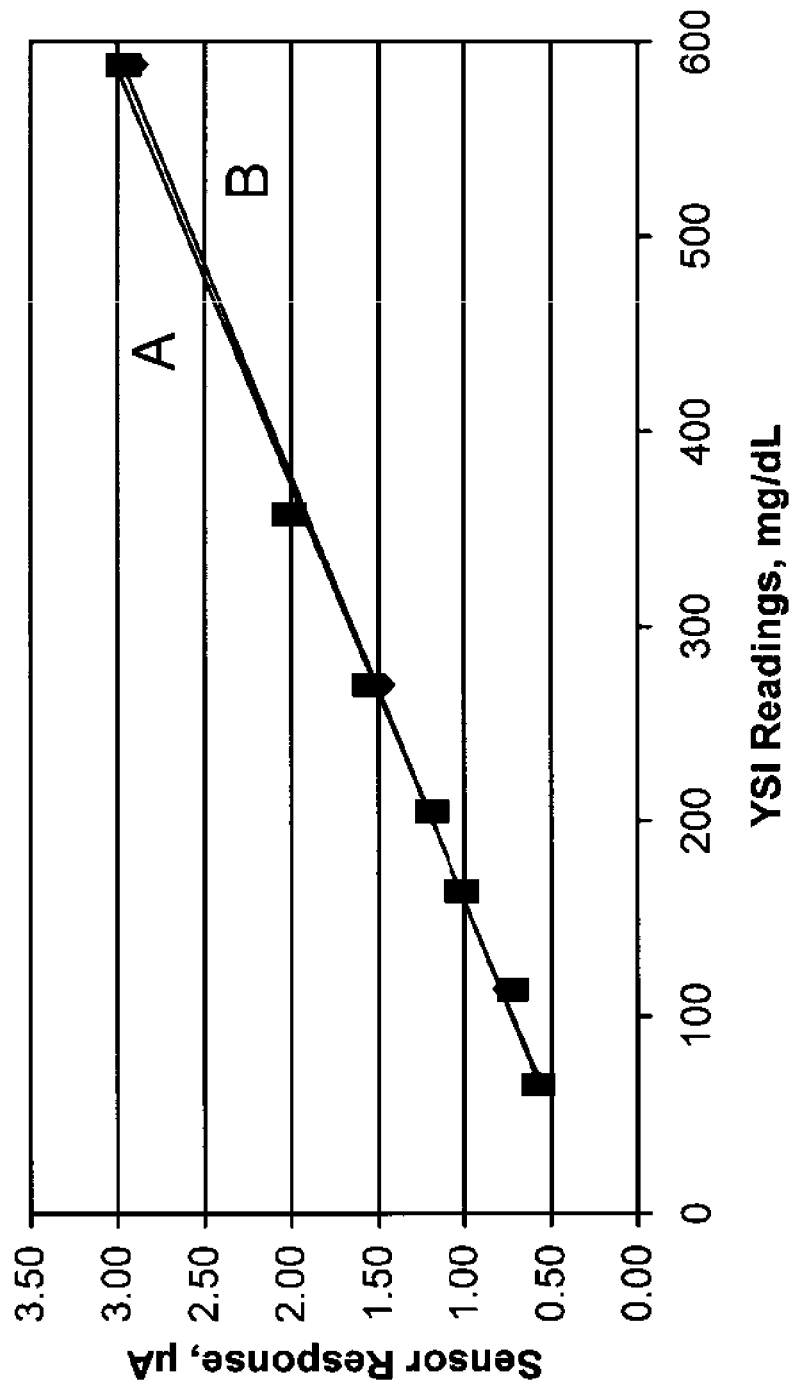

FIG. 23 shows the measured current response of the GDH-based electrode to varying glucose concentrations at $pO_2$ levels of 90 and 220 mmHg. The current responses at the GDH-based electrode are linear to the glucose concentration throughout the glucose concentration range tested for the oxygen level of 220 mmHg. As expected, there is substantially no difference between the current responses at $pO_2$ level of 90 mmHg and at $pO_2$ level of 220 mmHg throughout the glucose concentration range tested because of the inherent character of the GDH-based electrode.

EXAMPLE 2

Figure 24:
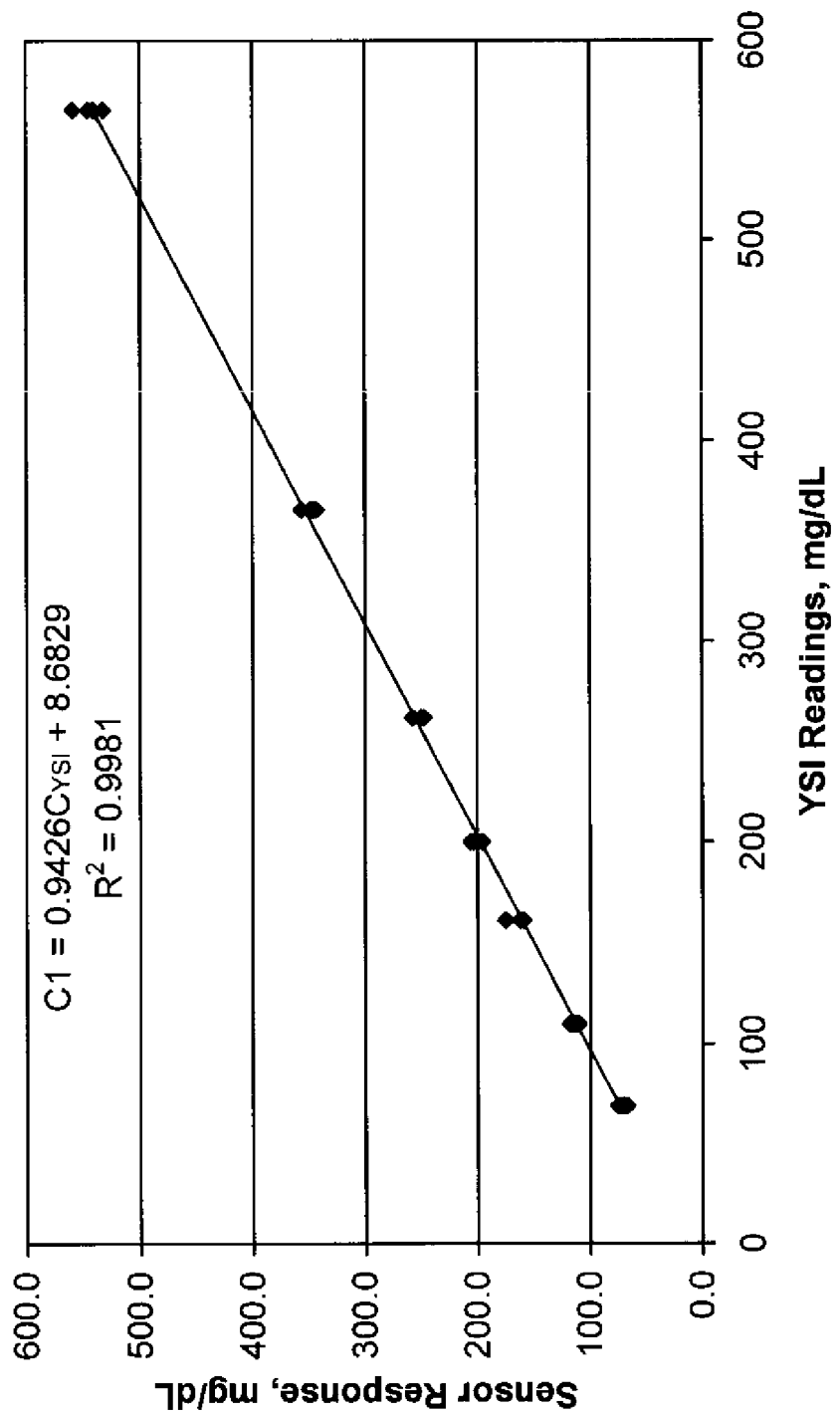
FIG. 24 illustrates the correlation of glucose concentration determined by the GOD-based electrode to that of a reference analyzer in a sample containing an oxygen level of 90 mm Hg.
Figure 25:
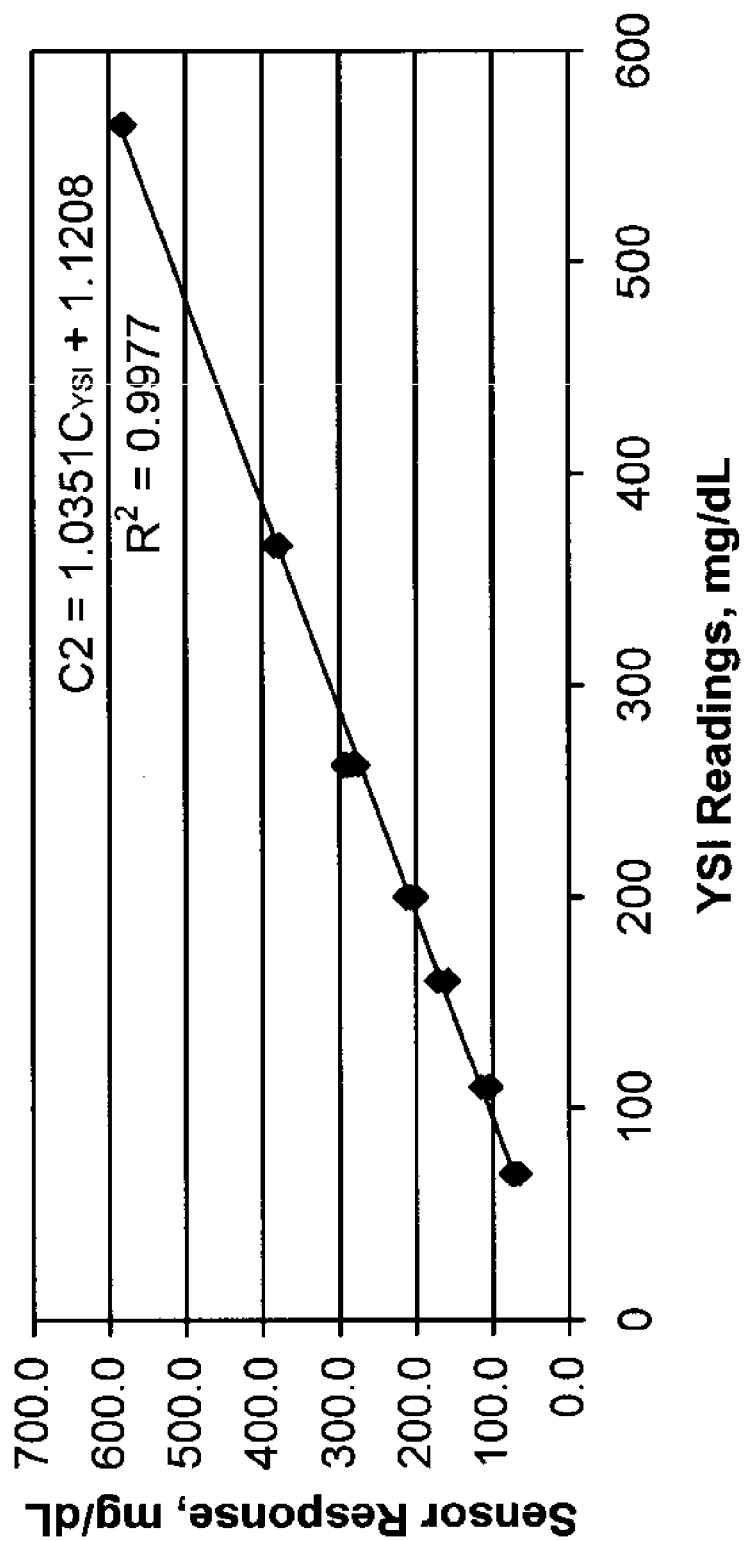
FIG. 25 illustrates the correlation of glucose concentration determined by the GDH-based electrode to that of a reference analyzer in a sample containing an oxygen level of 90 mm Hg.

Correlation Between Glucose Concentration Using the Glucose Strips and Glucose Readings at a Reference Analyzer The two working electrodes (W1 and W2) of the glucose strips were calibrated at $pO_2$ level of 90 mmHg using a reference analyzer (YSI Glucose Analyzer). The glucose concentrations (C1 and C2) resulting from the two working electrodes were plotted against the corresponding readings from the YSI Glucose Analyzer. The correlation plots are shown in FIGS. 24 and 25, respectively. The correlation equations and regression constants are given below:

$$\text{GOD-based electrode:} C1 = 0.9426 C_{YSI} + 8.6829, \quad R^2 = 0.9981 \tag{1}$$

$$\text{GDH-based electrode:} C2 = 1.0351 C_{YSI} + 1.1208, \quad R^2 = 0.9977 \tag{2}$$

It is obvious that the resulting concentrations from both working electrodes correlate well with the reference analyzer. As a result, either one can be used as a glucose sensor at an average $pO_2$ level of 90 mm Hg.

EXAMPLE 3

Demonstration of Selection of the Electrode Responses—Oxygen Effect

As the oxygen level of a real blood sample is unknown, one should take the advantage of GDH, which is virtually independent of oxygen concentration and preferably to be used for the determination of glucose. However, as discussed above, the GDH-based working electrode suffers from interference from other sugar, such as, galactose and maltose, which significantly increase the response and thus cause the glucose readings to be inaccurate (see below). In this case, the response from GOD-based working electrode has its advantage. Therefore, a predetermined value or cutoff is needed to decide which working electrode should be selected.

As mentioned above, the average change of the glucose concentration for the $pO_2$ varying from 30 to 90 mmHg is about 24.3 mg/dL at the GOD-based working electrode. This value was chosen as the predetermined value or cutoff value in determining the selection of which electrode response to use in determining the glucose concentration of the sample.

Table 1. Also listed is mean percentage error (MPE) against the reference analyzer (YSI Glucose Analyzer). The preferred glucose concentrations (C) is based on the predetermined value or cutoff value (24.3), which is also listed along with the resulting preferred MPEs. Note that the concentrations (C1 and C2) are calculated using calibration equations obtained at the oxygen level of 90 mm Hg.

TABLE 1

Testing Results at $pO_2$ of 30 mm Hg

| | GOD | | GDH | | | Preferred | |
| --- | --- | --- | --- | --- | --- | --- | --- |
| YSI | C1, mg/dL | MPE, % | C2, mg/dL | MPE, % | \|C1 − C2\| | C | MPE |
| 69 | 90.7 | 31.4 | 71.3 | 3.3 | 19.4 | C2 71.3 | 3.3 |
| 69 | 90.7 | 31.4 | 68.2 | 1.1 | 22.4 | C2 68.2 | 1.1 |
| 69 | 88.1 | 27.6 | 69.2 | 0.3 | 18.8 | C2 69.2 | 0.3 |
| 69 | 86.8 | 25.8 | 68.2 | 1.1 | 18.6 | C2 68.2 | 1.1 |
| 110 | 135.9 | 23.6 | 112.6 | 2.4 | 23.3 | C2 112.6 | 2.4 |
| 110 | 133.4 | 21.2 | 110.6 | 0.5 | 22.8 | C2 110.6 | 0.5 |
| 110 | 135.9 | 23.6 | 114.7 | 4.3 | 21.3 | C2 114.7 | 4.3 |
| 110 | 135.9 | 23.6 | 118.8 | 8.0 | 17.1 | C2 118.8 | 8.0 |
| 161 | 187.8 | 16.6 | 170.3 | 5.8 | 17.5 | C2 170.3 | 5.8 |
| 161 | 185.2 | 15.0 | 170.3 | 5.8 | 14.9 | C2 170.3 | 5.8 |
| 161 | 188.6 | 17.1 | 166.2 | 3.2 | 22.4 | C2 166.2 | 3.2 |
| 161 | 186.5 | 15.8 | 174.4 | 8.3 | 12.1 | C2 174.4 | 8.3 |
| 200 | 224.1 | 12.0 | 205.0 | 2.5 | 19.1 | C2 205.0 | 2.5 |
| 200 | 229.3 | 14.6 | 205.3 | 2.7 | 23.9 | C2 205.3 | 2.7 |
| 200 | 225.4 | 12.7 | 201.2 | 0.6 | 24.2 | C2 201.2 | 0.6 |
| 200 | 224.1 | 12.0 | 203.3 | 1.6 | 20.8 | C2 203.3 | 1.6 |
| 262 | 275.9 | 5.3 | 281.5 | 7.5 | 5.6 | C2 281.5 | 7.5 |
| 262 | 278.5 | 6.3 | 279.5 | 6.7 | 1.0 | C2 279.5 | 6.7 |
| 262 | 281.1 | 7.3 | 273.3 | 4.3 | 7.8 | C2 273.3 | 4.3 |
| 262 | 277.2 | 5.8 | 267.1 | 2.0 | 10.1 | C2 267.1 | 2.0 |
| 366 | 379.6 | 3.7 | 366.0 | 0.0 | 13.6 | C2 366.0 | 0.0 |
| 366 | 377.0 | 3.0 | 359.8 | 1.7 | 17.2 | C2 359.8 | 1.7 |
| 366 | 382.2 | 4.4 | 368.1 | 0.6 | 14.1 | C2 368.1 | 0.6 |
| 366 | 377.0 | 3.0 | 372.2 | 1.7 | 4.8 | C2 372.2 | 1.7 |
| 565 | 576.6 | 2.1 | 569.9 | 0.9 | 6.6 | C2 569.9 | 0.9 |
| 565 | 579.2 | 2.5 | 567.9 | 0.5 | 11.3 | C2 567.9 | 0.5 |
| 565 | 571.0 | 1.1 | 551.4 | 2.4 | 19.6 | C2 551.4 | 2.4 |
| 565 | 579.2 | 2.5 | 572.0 | 1.2 | 7.2 | C2 572.0 | 1.2 |
| Mean | | 13.3 | | 2.9 | | | 3.9 |

For example, if the absolute difference between C1 and C2 or |C1-C2|≦24.3 mg/dL, the preferred glucose concentration is equal to C2, i.e. the concentration determined from the GDH-based working electrode. Otherwise, the preferred glucose concentration is equal to C1, i.e. the concentration determined from the GOD-based working electrode. That means the preferred glucose readings for the sensor of the present invention is always from the GDH-based working electrode so long as there is no significant interference from other sugars such as galactose and maltose. It should be pointed out that the predetermined value or cutoff value "24.3" is not a fixed number. It is used for illustration purpose only. The value depends on the configuration of the electrodes and the composition of the reagent mixture. It also depends on the test error required for the measurement.

The selection between the two responses from the two working electrodes can be performed automatically when the glucose strips are used in connection with a preprogrammed testing device.

In order to demonstrate the discrimination feature of the glucose strip of the present invention against the influence of dissolved oxygen, blood samples at $pO_2$ level of 30 mmHg with seven levels of glucose concentration ranging from 69 to 565 mg/dL were tested with the glucose strips of the present invention. The glucose concentrations (C1 and C2) resulting from the two working electrodes (W1 and W2) are listed in As Illustrated in Table 1, the preferred mean MPE (3.9%) is significantly improved compared to the mean MPE (13.3%) resulting from the GOD-based working electrodes and is also comparable to the mean MPE (2.9%) resulting from the GDH-based working electrodes. The MPEs for the GDH-based working electrodes are within the acceptable range throughout the glucose concentration range, indicating no oxygen effect. However, The MPEs for the GOD-based working electrodes are much higher due to the oxygen effect, especially at low glucose concentrations. The unique feature of the sensor of the present invention substantially reduces the interference from oxygen by the selection between the two working electrodes.

EXAMPLE 4

Demonstration of Selection of the Electrode Responses—Interference from Maltose and Galactose In order to demonstrate the discriminating feature of the glucose measurement of the present invention against the interference from galactose and maltose, the blood samples at $pO_2$ level of 90 mmHg with two levels of glucose concentration were spiked with varying concentrations of galactose and maltose, respectively. The resulting blood samples were tested with the glucose strips of the present invention. The results are summarized in Tables 2 and 3.

TABLE 2

Testing Results for Galactose-Spiked Samples

| Galactose Spiked, mM | YSI, mg/dL | GDH C2, mg/dL | GDH MPE, % | GOD C1, mg/dL | GOD MPE, % | \|C1 − C2\| | Preferred | C, mg/dL | MPE, % |
|---|---|---|---|---|---|---|---|---|---|
| 0 | 73 | 72.9 | 0.2 | 74.0 | 1.4 | 1.1 | C2 | 72.9 | 0.2 |
|  | 198 | 196.1 | 1.0 | 193.6 | 2.2 | 2.5 | C2 | 196.1 | 1.0 |
| 1 | 73 | 98.6 | 35.1 | 73.0 | 0.0 | 25.6 | C1 | 73.0 | 0.0 |
|  | 197 | 221.5 | 12.5 | 196.2 | 0.4 | 25.3 | C1 | 196.2 | 0.4 |
| 2 | 72 | 130.6 | 81.3 | 75.1 | 4.3 | 55.5 | C1 | 75.1 | 4.3 |
|  | 197 | 258.9 | 31.4 | 192.3 | 2.4 | 66.6 | C1 | 192.3 | 2.4 |
| 5 | 71 | 169.7 | 139.0 | 72.5 | 2.1 | 97.2 | C1 | 72.5 | 2.1 |
|  | 196 | 289.8 | 47.8 | 188.4 | 3.9 | 101.4 | C1 | 188.4 | 3.9 |
| Mean |  |  | 43.5 |  | 2.1 |  |  |  | 1.8 |

Table 2 depicts the absolute concentration difference |C1-C2|, as well as preferred glucose concentrations (C) and the resulting MPEs. The preferred glucose concentration is based on the predetermined value or cutoff value (24.3). The preferred mean MPE (1.8%) is much smaller than the mean MPE (43.5%) resulting from the GDH-based working electrodes and is also comparable to the mean MPE (2.1%) resulting from the GOD-based on working electrodes.

TABLE 3

Testing Results for Maltose-Spiked Samples

| Maltose Spiked, mM | YSI, mg/dL | GDH C2, mg/dL | GDH MPE, % | GOD C1, mg/dL | GOD MPE, % | \|C1 − C2\| | Preferred | C, mg/dL | MPE, % |
|---|---|---|---|---|---|---|---|---|---|
| 0 | 67 | 68.0 | 1.5 | 69.0 | 3.0 | 1.0 | C2 | 68.0 | 1.5 |
|  | 212 | 210.0 | 0.9 | 216.0 | 1.9 | 6.0 | C2 | 210.0 | 0.9 |
| 1 | 68 | 100.5 | 47.8 | 69.0 | 1.5 | 31.5 | C1 | 69.0 | 1.5 |
|  | 208 | 253.8 | 22.0 | 209.0 | 0.5 | 44.8 | C1 | 209.0 | 0.5 |
| 2 | 67 | 134.5 | 100.7 | 70.0 | 4.5 | 64.5 | C1 | 70.0 | 4.5 |
|  | 210 | 308.0 | 46.7 | 202.0 | 3.8 | 106.0 | C1 | 202.0 | 3.8 |
| 5 | 66 | 184.8 | 180.0 | 65.0 | 1.5 | 119.8 | C1 | 65.0 | 1.5 |
|  | 210 | 366.0 | 74.3 | 199.0 | 5.2 | 167.0 | C1 | 199.0 | 5.2 |
| Mean |  |  | 59.2 |  | 2.7 |  |  |  | 2.4 |

Table 3 depicts the absolute concentration difference |C1-C2|, as well as preferred glucose concentrations (C) and the resulting MPEs. The preferred glucose concentration is based on the predetermined value or cutoff value (24.3). The preferred mean MPE (2.4%) is much smaller than the mean MPE (59.2%) resulting from the GDH-based working electrodes and is also comparable to the mean MPE (2.7%) resulting from the GOD-based on working electrodes.

As expected, the GDH-based working electrodes are subjected to severe interference from galactose and maltose, while these compounds have no effect on the GOD-based working electrodes. It is preferred to use the response from the GOD-based working electrode when a sample contains galactose or/and maltose. The unique feature of the sensor of the present invention substantially reduces the effect of the interfering sugars by the selection between the two working electrodes.

The above examples illustrate the interference effects from oxygen and from interfering sugars in connection with the use of the glucose strips of the present invention. A real sample could have both oxygen and galactose/maltose issues. These issues can also be resolved using the selection feature and the two working electrodes of the glucose sensor of the present invention.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A glucose biosensor comprising:
  a laminated body having a fluid sample inlet end and an electrical contact end;
  a fluid sample inlet;
  a substantially flat sample chamber in communication between said fluid sample inlet and a vent opening, said sample chamber being adapted to collect a fluid sample through said fluid sample inlet;
  a GOD-based glucose electrode;
  a GDH-based glucose electrode; and
  a reference electrode wherein said GOD-based glucose electrode, said GDH-based glucose electrode and said reference electrode are within said sample chamber.

2. The glucose biosensor of claim 1 wherein said GOD-based glucose electrode further includes a redox mediator.

3. The glucose biosensor of claim 2 wherein said GOD-based glucose electrode further includes one or more of a material selected from the group consisting of a binder, a buffer and a surfactant.

4. The glucose biosensor of claim 1 wherein said GDH-based glucose electrode further includes a redox mediator.

5. The glucose biosensor of claim 4 wherein said GDH-based glucose electrode further includes one or more of a material selected from the group consisting of a binder, a buffer and a surfactant.

6. A system for more accurately measuring glucose in a sample comprising:

a first glucose-sensing electrode incorporating a quantity of glucose oxidase;

a second glucose-sensing electrode incorporating a quantity of glucose dehydrogenase;

a reference electrode; and means for selecting between a first glucose measurement made with said first glucose-sensing electrode in a sample and a second glucose measurement made with said second glucose-sensing electrode in said sample.

7. The system of claim 6 wherein said first glucose-sensing electrode further includes a redox mediator.

8. The system of claim 7 wherein said first glucose-sensing electrode further includes one or more of a material selected from the group consisting of a binder, a buffer and a surfactant.

9. The system of claim 6 wherein said second glucose-sensing electrode further includes a redox mediator.

10. The system of claim 9 wherein said first glucose-sensing electrode further includes one or more of a material selected from the group consisting of a binder, a buffer and a surfactant.

11. The system of claim 6 wherein said selecting means includes a system capable of determining the difference between said first glucose measurement and said second glucose measurement and selecting one of said first glucose measurement and said second glucose measurement based on said difference when said difference is compared to a predefined value.

12. A method for determining glucose concentration in a blood sample more accurately, said method comprising:

making a first measurement of said glucose concentration of said blood sample using a first glucose electrode incorporating glucose oxidase;

making a second measurement of said glucose concentration of said blood sample using a second glucose electrode incorporating glucose dehydrogenase;

calculating the difference between said first measurement and said second measurement; and selecting one of said first measurement and said second measurement based on said calculated difference when said difference is compared to a predefined value.

13. The method of claim 12 wherein said selecting step further includes selecting said first measurement if said calculated difference is greater than said predefined value.

14. The method of claim 12 wherein said selecting step further includes selecting said second measurement if said calculated difference is less than or equal to said predefined value.

15. A disposable glucose sensor comprising:

a sensor body having an open well forming a test chamber;

a GOD-based glucose electrode, a GDH-based glucose electrode and reference/counter electrode disposed within said open well; and electrical contacts on one end of said sensor body.

* * * * *